(12) United States Patent
Lim et al.

(10) Patent No.: US 9,936,933 B2
(45) Date of Patent: Apr. 10, 2018

(54) X-RAY APPARATUS

(71) Applicant: SAMSUNG ELECTRONICS CO., LTD., Suwon-si (KR)

(72) Inventors: Jae-guyn Lim, Seongnam-si (KR); Sung-ho Chang, Hwaseong-si (KR); Eung-bum Kim, Hwaseong-si (KR); Woo-young Jang, Seongnam-si (KR); Wan-hee Chun, Seongnam-si (KR); Hyun Choi, Yongin-si (KR); Woo-sup Han, Yongin-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 202 days.

(21) Appl. No.: 14/794,180

(22) Filed: Jul. 8, 2015

(65) Prior Publication Data

US 2016/0007950 A1    Jan. 14, 2016

(30) Foreign Application Priority Data

Jul. 11, 2014 (KR) ........................ 10-2014-0087323

(51) Int. Cl.
*A61B 6/00* (2006.01)
*A61B 6/06* (2006.01)
(Continued)

(52) U.S. Cl.
CPC ............ *A61B 6/548* (2013.01); *A61B 5/0044* (2013.01); *A61B 5/061* (2013.01); *A61B 6/06* (2013.01);
(Continued)

(58) Field of Classification Search
CPC ... A61B 5/0037; A61B 5/0044; A61B 5/0402; A61B 5/061; A61B 6/06; A61B 6/08;
(Continued)

(56) References Cited

U.S. PATENT DOCUMENTS 5,278,887 A    1/1994   Chiu et al.
6,050,267 A    4/2000   Nardella et al.
(Continued)

FOREIGN PATENT DOCUMENTS

EP    0915675 B1    10/2008
JP    2001-522288 A    11/2001
(Continued)

OTHER PUBLICATIONS

Communication dated Mar. 31, 2015 by the International Searching Authority in related Application No. PCT/KR2014/010000, (PCT/ISA 210 and PCT/ISA/237)

*Primary Examiner* — Irakli Kiknadze
(74) *Attorney, Agent, or Firm* — Sughrue Mion, PLLC

(57) ABSTRACT

An X-ray apparatus includes: a collimator for adjusting an X-ray irradiation region; a data obtainer for obtaining position information of a target in an object based on an electrode signal sensed from electrodes attached to the object; and a controller for setting first coordinates indicating a position of the target on a first coordinate system with respect to the object based on the position information, transforming the first coordinates to second coordinates on a second coordinate system with respect to an X-ray image of the object, and adjusting a position of the collimator based on the second coordinates.

21 Claims, 19 Drawing Sheets

(51) Int. Cl.
*A61B 6/12* (2006.01)
*A61B 6/08* (2006.01)
*A61B 5/06* (2006.01)
*A61B 5/00* (2006.01)
*A61B 5/0402* (2006.01)

(52) U.S. Cl.
CPC .............. *A61B 6/08* (2013.01); *A61B 6/12* (2013.01); *A61B 6/4417* (2013.01); *A61B 6/4476* (2013.01); *A61B 6/469* (2013.01); *A61B 6/487* (2013.01); *A61B 6/504* (2013.01); *A61B 6/545* (2013.01); *A61B 6/563* (2013.01); *A61B 6/566* (2013.01); *A61B 6/587* (2013.01); *A61B 6/589* (2013.01); *A61B 5/0037* (2013.01); *A61B 5/0402* (2013.01); *A61B 6/4441* (2013.01); *A61B 6/503* (2013.01); *A61B 6/542* (2013.01); *A61B 6/583* (2013.01)

(58) Field of Classification Search
CPC ....... A61B 6/12; A61B 6/4417; A61B 6/4441; A61B 6/4476; A61B 6/469; A61B 6/487; A61B 6/503; A61B 6/504; A61B 6/542; A61B 6/545; A61B 6/548; A61B 6/563; A61B 18/1492; A61B 2017/00026; A61B 2017/00088; A61B 2017/00092; A61B 2018/00357; A61B 2018/00577; A61B 2034/2051; A61B 2090/376; A61B 5/0538; A61B 5/062; A61B 5/063; A61B 5/6876

USPC .................... 378/62, 145, 147, 151, 164, 19
See application file for complete search history.

(56) References Cited

U.S. PATENT DOCUMENTS

| | | | |
|---|---|---|---|
| 7,340,033 B2 | 3/2008 | Mollus et al. | |
| 8,106,905 B2 | 1/2012 | Markowitz et al. | |
| 8,445,878 B2 | 5/2013 | Guez | |
| 2007/0165779 A1* | 7/2007 | Chen | A61N 5/1049 378/65 |
| 2010/0183115 A1* | 7/2010 | Van Stevendaal | G01N 23/046 378/6 |
| 2010/0317981 A1* | 12/2010 | Grunwald | A61B 5/04017 600/509 |
| 2012/0059270 A1 | 3/2012 | Grunwald | |
| 2013/0077745 A1* | 3/2013 | Wang | A61B 6/52 378/62 |
| 2014/0024920 A1 | 1/2014 | Paitel et al. | |
| 2014/0180062 A1 | 6/2014 | Amit | |

FOREIGN PATENT DOCUMENTS

| | | |
|---|---|---|
| JP | 4265698 B2 | 5/2009 |
| JP | 5342628 B2 | 11/2013 |
| KR | 10-2012-0027527 A | 3/2012 |

\* cited by examiner

X-RAY APPARATUS

CROSS-REFERENCE TO RELATED APPLICATION

This application claims priority from Korean Patent Application No. 10-2014-0087323, filed on Jul. 11, 2014, in the Korean Intellectual Property Office, the disclosure of which is incorporated herein in its entirety by reference.

BACKGROUND

1. Field

Apparatuses and methods consistent with exemplary embodiments relate to an X-ray apparatus, and more particularly, to an X-ray apparatus that adjusts a collimator of the X-ray apparatus by tracking a position of a target.

2. Description of the Related Art

An X-ray apparatus acquires images of internal structures of the human body by transmitting an X-ray through the human body. The X-ray apparatus may acquire medical images of an object in a simpler manner and within a shorter time than other medical imaging apparatuses such as a magnetic resonance imaging (MRI) apparatus and a computed tomography (CT) apparatus. Therefore, the X-ray apparatus is widely used in imaging of chest, abdomen, skeleton, nasal sinuses, neck soft tissue, breast, etc.

Fluoroscopy is an image processing technique of acquiring an X-ray video by imaging an object in real time and may be used in angiography. For example, a user may use fluoroscopy in order to monitor X-ray angiography, surgical treatment, or the like.

The X-ray imaging including fluoroscopy uses radiation, and, thus, a user has to adjust a radiation dose to which an object is exposed. In particular, fluoroscopy requires X-ray imaging to be performed for a relatively long period of time, and thus various techniques to minimize a radiation dose are being developed. For example, a technique of obtaining a plurality of low-quality frames by X-ray imaging using a low dose of radiation and combining the low-quality frames to restore image quality is available. In addition, a dynamic region of interest (ROI) technique whereby a dose of radiation may be minimized by radiating an X-ray only to regions around an object is available.

However, there is a need for an X-ray apparatus that is capable of minimizing an amount of radiation to which an object is exposed and efficiently adjusting an ROI according to the intention of a user, so that the user may concentrate on a medical treatment.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more exemplary embodiments include an X-ray apparatus capable of minimizing an amount of radiation to which an object is exposed, by adjusting a collimator based on a position of a target.

One or more exemplary embodiments include an X-ray apparatus capable of minimizing an amount of radiation radiated to an object by accurately irradiating an X-ray to the object which is to be captured.

According to one or more exemplary embodiments, an X-ray apparatus includes: a collimator for adjusting an X-ray irradiation region; a data obtainer for obtaining position information of a target in an object based on an electrode signal sensed from a plurality of electrodes attached to the object; and a controller for setting first coordinates indicating a position of the target on a first coordinate system with respect to the object based on the position information, transforming the first coordinates to second coordinates on a second coordinate system with respect to an X-ray image of the object, and adjusting a position of the collimator based on the second coordinates.

The data obtainer may include a plurality of electrodes for electrocardiography (ECG) that are attached to the object, wherein the electrode signal is an electrocardiogram signal.

The data obtainer may measure impedance of the object included in an ROI based on the electrode signal and obtains the position information based on the impedance of the object.

The data obtainer may measure impedance of the object included in an ROI based on the electrode signal, generate an impedance map of the object based on the impedance of the object, and obtain the position information based on the impedance map of the object.

The controller may set the first coordinates to a three-dimensional (3D) rectangular coordinate system based on the electrode signal sensed from a plurality of electrodes attached to positions corresponding to three axes that are orthogonal to one another, set the second coordinate system to a two-dimensional (2D) rectangular coordinate system which is a plane perpendicular to an X-ray irradiation direction, and set a point on the plane that is closest to the first coordinates as the second coordinates.

The controller may set the first coordinate system to a 3D rectangular coordinate system based on the electrode signal sensed from the plurality of electrodes attached to positions corresponding to three axes that are orthogonal to one another, and set the second coordinate system to a 3D rectangular coordinate system including an axis in the same direction as an X-ray irradiation direction.

The target may be a tip of a catheter inserted in the object.

The X-ray apparatus may further include: an X-ray source for emitting an X-ray to the object; a detector for detecting an X-ray transmitted through the object; and a C-arm for connecting the X-ray source and the detector, wherein, based on an angle of the C-arm and the position information, the controller sets first coordinates indicating a position of the target on a first coordinate system with respect to the object, transforms the first coordinates to second coordinates on a second coordinate system with respect to an X-ray image of the object, and adjusts a position of the collimator based on the second coordinates.

The controller may adjust a position of the collimator based on a direction in which the second coordinates move.

The controller may automatically adjust an ROI based on a position of the collimator, and generates a third X-ray image by combining a first X-ray image captured before the ROI is adjusted and a second X-ray image captured after the ROI is adjusted.

The controller may generate a fluoroscopy that tracks a target based on the first coordinate, the second coordinate, and the collimator.

The controller may adjust an intensity of an X-ray based on the X-ray irradiation region adjusted by the collimator.

The controller may adjust an irradiation timing of an X-ray based on a control timing of the collimator.

According to one or more exemplary embodiments, an X-ray apparatus includes: a collimator for adjusting an X-ray irradiation region; and a controller for obtaining position information of a target in an object based on an electrode signal sensed from a plurality of electrodes attached to the object and adjusting a position of the collimator based on the position information of the target.

The plurality of electrodes may include a plurality of electrodes for ECG that are attached to the object, and the electrode signal is an electrocardiogram signal.

The target may be a tip of a catheter inserted in the object.

The X-ray apparatus may further include: an X-ray source for emitting an X-ray to the object; a detector for detecting an X-ray transmitting through the object; and a C-arm for connecting the X-ray source and the detector, wherein the controller adjusts a position of the collimator based on an angle of the C-arm and position information of the target.

The controller may adjust a position of the collimator based on a direction in which the target moves.

The controller may automatically adjust an ROI based on a position of the collimator, and generates a third X-ray image by combining a first X-ray image captured before the ROI is adjusted and a second X-ray image captured after the ROI is adjusted.

The controller may generate a fluoroscopy that tracks a target based on the first coordinate, the second coordinate, and the collimator.

The controller may adjust an intensity of an X-ray based on the X-ray irradiation region adjusted by the collimator.

The controller may adjust an irradiation timing of an X-ray based on a control timing of the collimator.

BRIEF DESCRIPTION OF THE DRAWINGS

The above and/or other aspects will become more apparent by describing certain exemplary embodiments with reference to the accompanying drawings, in which.

DETAILED DESCRIPTION

Figure 1:
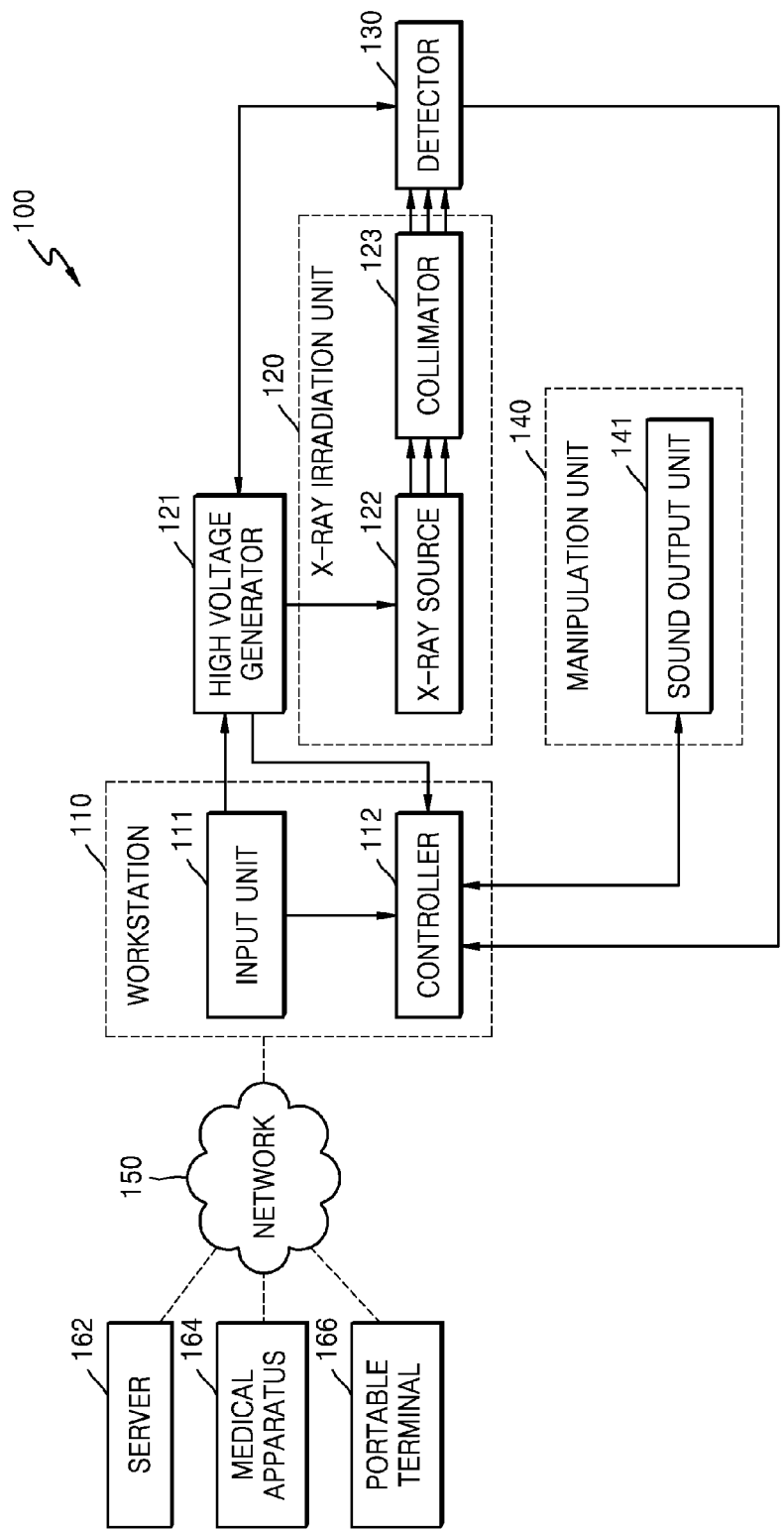
FIG. 1 is a block diagram illustrating a structure of an X-ray apparatus according to an exemplary embodiment.

Certain exemplary embodiments are described in greater detail below with reference to the accompanying drawings.

In the following description, the same drawing reference numerals are used for the same elements even in different drawings. Thus, description of the same elements is not repeated. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

As used herein, the term "and/or" includes any and all combinations of one or more of the associated listed items. Expressions such as "at least one of," when preceding a list of elements, modify the entire list of elements and do not modify the individual elements of the list.

Throughout the specification, an "image" may denote multi-dimensional data composed of discrete image elements (for example, pixels in a 2D image and voxels in a 3D image). For example, an image may include medical images of an object acquired by an X-ray, a CT, an MRI, an ultrasound, and other medical image systems.

Furthermore, in the present specification, an "object" may be a human, an animal, or a part of a human or animal. For example, the object may be an organ (e.g., the liver, the heart, the womb, the brain, a breast, or the abdomen), a blood vessel, or a combination thereof. Furthermore, the "object" may be a phantom. The phantom means a material having a density, an effective atomic number, and a volume that are approximately the same as those of an organism. For example, the phantom may be a spherical phantom having properties similar to the human body.

Furthermore, in the present specification, a "user" may be, but is not limited to, a medical expert, such as a medical doctor, a nurse, a medical laboratory technologist, or a technician who repairs a medical apparatus.

FIG. 1 is a block diagram of an X-ray apparatus 100. The X-ray apparatus 100 shown in FIG. 1 may be a fixed-type X-ray apparatus or a mobile X-ray apparatus.

Referring to FIG. 1, the X-ray apparatus 100 includes a workstation 110, an X-ray irradiation unit 120, a high voltage generator 121, and a detector 130.

The workstation 110 includes an input unit 111 through which a user may input commands for manipulating the X-ray apparatus 100 including an X-ray irradiation, and a controller 112 controlling overall operations of the X-ray apparatus 100.

The high voltage generator 121 generates a high voltage for generating X-rays, and applies the high voltage to an X-ray source 122.

The X-ray irradiation unit 120 includes the X-ray source 122 receiving the high voltage applied from the high voltage generator 121 to generate and irradiate the X-ray, and a collimator 123 for guiding a path of the X-ray irradiated from the X-ray source 122.

The detector 130 detects an X-ray that is radiated from the X-ray radiator 120 and has been transmitted through an object.

The X-ray apparatus 100 may further include a manipulation unit 140 including a sound output unit 141 outputting sound representing information relating to imaging operation such as the X-ray irradiation under a control of the controller 112.

The workstation 110, the X-ray irradiation unit 120, the high voltage generator 121, and the detector 130 may be connected to each other via wires or wirelessly. In the case of the wireless connection, a device (not shown) for synchronizing clocks with each other may be further included.

The input unit 111 may include a keyboard, a mouse, a touch screen, a voice recognizer, a fingerprint recognizer, an iris recognizer, and other appropriate devices known to those skilled in the art. The user may input a command for irradiating the X-ray via the input unit 111, and the input unit 111 may include a switch for inputting the command. The switch may be configured so that an irradiation command for irradiating the X-ray may be input only when the switch is pushed twice.

That is, when the user pushes the switch, a prepare command for performing a pre-heating operation for X-ray irradiation may be input through the switch, and then, when the user pushes the switch once more, the irradiation command for irradiating the X-ray may be subsequently input through the switch. When the user manipulates the switch as described above, the input unit 111 generates signals corresponding to the commands input through the switch manipulation, that is, a prepare signal and an irradiation signal, and outputs the generated signals to the high voltage generator 121 generating a high voltage for generating the X-ray.

When the high voltage generator 121 receives the prepare signal output from the input unit 111, the high voltage generator 121 starts a pre-heating operation, and when the pre-heating is finished, the high voltage generator 121 outputs a ready signal to the controller 121. The detector 130 also needs to prepare for detecting the X-ray, and thus, when the high voltage generator 121 receives the prepare signal output from the input unit 111, the high voltage generator 121 outputs a prepare signal to the detector 130 at the same time of performing the pre-heating operation, so that the detector 130 may prepare for detecting the X-ray transmitted through the object. The detector 130 prepares for detecting the X-ray when receiving the prepare signal, and when the preparing for the detection is finished, the detector 130 outputs a ready signal to the high voltage generator 121 and the controller 112.

When the pre-heating operation of the high voltage generator 121 is finished, the detector 130 is ready for the detecting the X-ray, and the irradiation signal is output from the input unit 111 to the high voltage generator 121, the high voltage generator 121 generates and applies the high voltage to the X-ray source 122, and the X-ray source 122 irradiates the X-ray.

When the irradiation signal is output from the input unit 111, the controller 112 may output a sound output signal to the sound output unit 141 so that the sound output unit 141 outputs predetermined sound and the object may recognize the irradiation of X-ray. The sound output unit 141 may output sound representing other information relating to the imaging, in addition to the X-ray irradiation. In FIG. 1, the sound output unit 141 is included in the manipulation unit 140; however, the exemplary embodiments, and the sound output unit 140 may be located at a different location from the manipulation unit 140. For example, the sound output unit 141 may be included in the workstation 110, or may be located on a wall surface of an examination room in which the X-ray imaging of the object is performed.

The controller 112 controls locations of the X-ray irradiation unit 120 and the detector 130, an imaging timing, and imaging conditions according to imaging conditions set by the user.

In more detail, the controller 112 controls the high voltage generator 121 and the detector 130 according to the command input via the input unit 111 to control an irradiation timing of the X-ray, an intensity of the X-ray, and an irradiation region of the X-ray. The controller 112 adjusts the location of the detector 130 according to a predetermined imaging condition, and controls an operation timing of the detector 130.

The controller 112 generates a medical image of the object by using image data transmitted from the detector 130. In detail, the controller 121 receives the image data from the detector 130, and generates the medical image of the object by removing noise in the image data, and adjusting a dynamic range and interleaving of the image data.

The X-ray apparatus 100 shown in FIG. 1 may further include an output unit (not shown) for outputting the medical image generated by the controller 112. The output unit may output information for the user to manipulate the X-ray apparatus 100, for example, a user interface (UI), user information, or object information. The output unit may include a printer, a cathode ray tube (CRT) display, a liquid crystal display (LCD), a plasma display panel (PDP), an organic light emitting diode (OLED) display, a field emission display (FED), a light emitting diode (LED) display, a vacuum fluorescent display (VFD), a digital light processing (DLP) display, a primary flight display (PFD), a 3D display, a transparent display, and other various output devices known to those skilled in the art.

The workstation 110 shown in FIG. 1 may further include a communicator (not shown) that may be connected to an external server 162, an external medical apparatus 164, and an external portable terminal 166 via a network 150.

The communicator may be connected to the network 150 via wires or wirelessly to communicate with the external server 162, the external medical apparatus 164, or the external portable terminal 166. The communicator may transmit or receive data relating to diagnostics of the object via the network 150, and may transmit or receive medical images captured by the external medical apparatus 164, for example, a CT, an MRI, or another X-ray apparatus. Moreover, the communicator may receive medical history or treatment schedule of an object, e.g., a patient, from the external server 162 to diagnose a disease of the object. The communicator may perform data communication with the external portable terminal 166 such as a mobile phone of a doctor or a patient, a personal digital assistant (PDA), or a laptop computer, as well as the external server 162 or the external medical apparatus 164 in a hospital.

The communicator may include one or more elements enabling to communicate with external apparatuses, for example, a short distance communication module, a wired communication module, and a wireless communication module.

The short distance communication module is a module for communicating with a device located within a predetermined distance. The short distance communication technology may be wireless local area network (LAN), Wi-Fi, Bluetooth, Zigbee, Wi-Fi Direct (WFD), ultra wideband (UWD), infrared data association (IrDA), Bluetooth low energy (BLE), near field communication (NFC), or the like; however, the exemplary embodiments are not limited thereto.

The wired communication module is a module for communicating by using an electrical signal or an optical signal, and the wired communication technology may be wired communication technology using a paired cable, a coaxial cable, or an optical fiber cable, and a wired communication technology that is known to those skilled in the art.

The wireless communication module may transmit and/or receive a wireless signal to and from at least one of a base, an external device, and a server in a mobile communication network. The wireless signal may be a voice call signal, a video call signal, or various types of data according to text/multimedia messages transmission.

The X-ray apparatus 100 shown in FIG. 1 may include a plurality of digital signal processors (DSPs), an ultra-small calculator, and a processing circuit for specialized usage, for example, a high speed analog/digital (A/D) conversion, a high speed Fourier transformation, an array process, etc.

The communication between the workstation 110 and the X-ray generator 120, the workstation 110 and the high voltage generator 211, and the workstation 110 and the detector 130 may use a high speed digital interface, such as low voltage differential signaling (LVDS), asynchronous serial communication, such as universal asynchronous receiver transmitter (UART), synchronous serial communication, or a low latency network protocol, such as a controller area network (CAN), and other various communication methods that are known to those skilled in the art may be used.

Examples of the tracking ROI may include a method of tracking an object based on an image variation between captured fluoroscopy frames, a method of attaching an electromagnetic apparatus to a tip of a catheter and tracking the catheter by using an electromagnetic field generated in the electromagnetic apparatus, etc.

Hereinafter, an X-ray apparatus capable of adjusting a collimator while tracking a target based on an electrode signal, according to an exemplary embodiment, will be described in detail.

Figure 2:
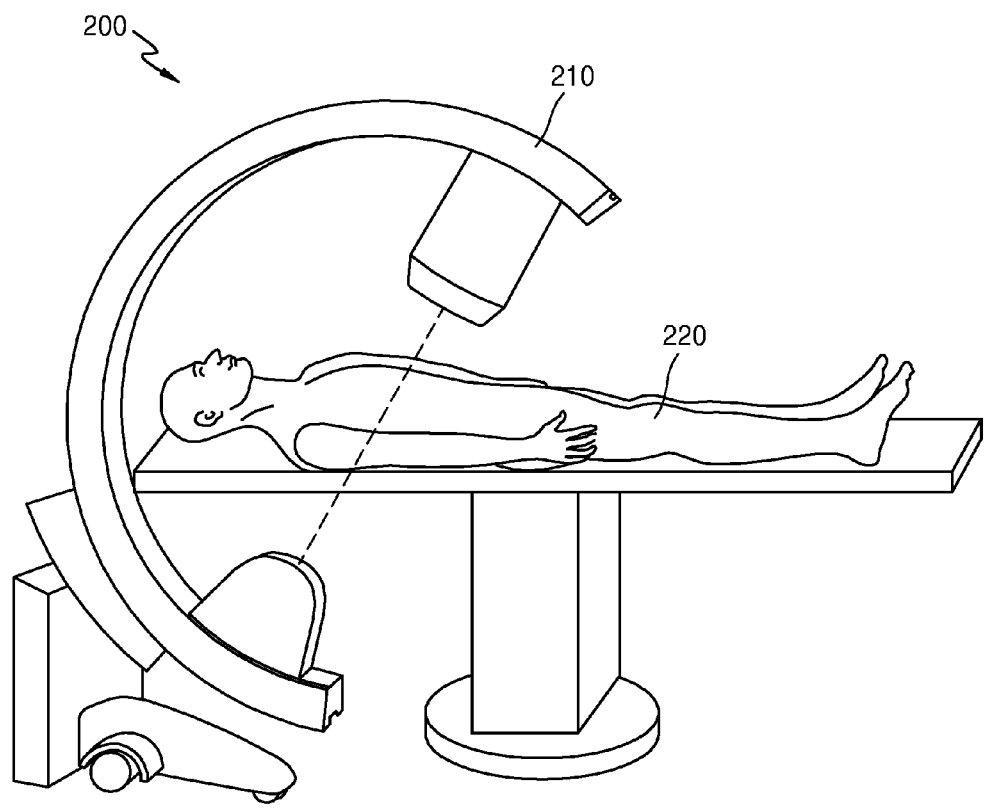
FIG. 2 illustrates a C-arm X-ray apparatus to which an X-ray apparatus according to an exemplary embodiment.

FIG. 2 illustrates a C-arm X-ray apparatus 200 according to an exemplary embodiment.

A user may image an object 220 at various positions or at various angles by using a C-arm 210. For example, the user may rotate the C-arm 210 or move the C-arm 210 vertically or horizontally to image an ROI of the object 220 to acquire a fluoroscopy image. Thus, the user may efficiently capture an image of an object by using the C-arm X-ray apparatus 200.

A C-arm X-ray apparatus may be useful in X-ray angiography or medical treatments, such as surgical operations, where an X-ray image of an object is to be continuously checked during treatment, and a fluoroscopy image is to be acquired by continuously irradiating an X-ray to the object.

For example, in angiography, a guide wire may be installed on a portion of an object to perform X-ray imaging or a thin needle may be used to inject medicine to perform X-ray imaging.

Alternatively, in surgical treatments, when conducting a treatment that involves inserting a catheter, a stent, a needle, or the like into the body, a user, i.e., a doctor, has to check whether the catheter or the like is inserted exactly into a target point of an object. Thus, the user may acquire a fluoroscopy image during treatment, and may conduct the treatment by checking a position of a target such as the catheter by viewing the acquired fluoroscopy image.

In the present exemplary embodiment, when a conductive material such as a guide wire, a needle, a catheter or a stent is installed on or inserted into a portion of an object, an X-ray of the portion of the object is captured by using a C-arm X-ray apparatus. Thus, according to the present exemplary embodiment, an object to which an X-ray is irradiated may be accurately detected and a position and/or a size of a collimator of the C-arm X-ray apparatus may be exactly adjusted according to portions of the object for which imaging is needed.

Figure 3:
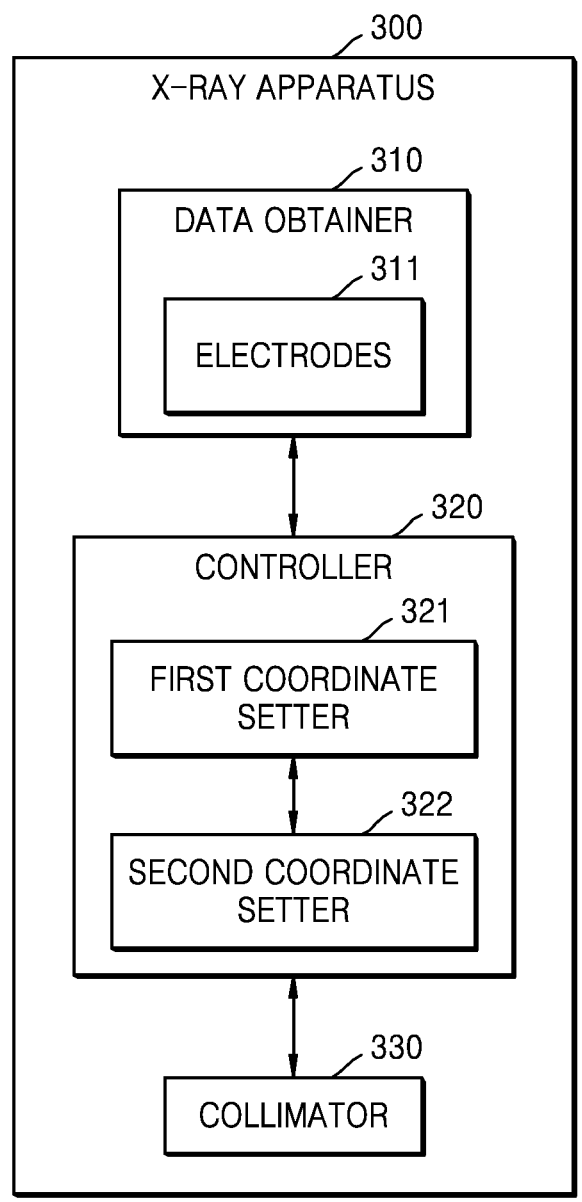
FIG. 3 illustrates a structure of an X-ray apparatus according to an exemplary embodiment.

FIG. 3 illustrates an X-ray apparatus 300 according to an exemplary embodiment.

The X-ray apparatus 300 according to an exemplary embodiment includes a data obtainer 310, a controller 320, and a collimator 330.

The collimator 330 adjusts an X-ray irradiation region.

The data obtainer 310 obtains position information of a target in an object based on an electrode signal sensed from a plurality of electrodes 311 attached to the object.

The controller 320 sets first coordinates indicating a position of a target on a first coordinate system with respect to an object based on position information of the target, transforms the first coordinates to second coordinates on a second coordinate system with respect to an X-ray image of the object, and adjusts a position of the collimator 330 based on the second coordinates.

The controller 320 may include a first coordinate setter 321 setting first coordinates indicating a position of a target with respect to an object and a second coordinate setter 322 setting second coordinates indicating a position of a target with respect to an X-ray image.

The X-ray apparatus 300 illustrated in FIG. 3 may be included in or correspond to the X-ray apparatus 100 illustrated in FIG. 1. In detail, the controller 320 and the collimator 330 may respectively correspond to the controller 112 and the collimator 123 of FIG. 1. The data obtainer 310 and the plurality of electrodes 311 may be included in the workstation 110 of FIG. 1. Accordingly, descriptions provided with reference to FIG. 1 and also applied to the X-ray apparatus 300 will be omitted.

According to an exemplary embodiment, the data obtainer 310 of the X-ray apparatus 300 may obtain position information of a target related to a position of a target in an object. For example, position information may be at least one of an electrode signal sensed from a plurality of electrodes, impedance or an impedance map of an object obtained from an electrode signal, and predetermined information obtained by processing an impedance map.

For example, the data obtainer 310 may obtain position information of a target based on an electrode signal sensed from a plurality of electrodes.

Alternatively, the data obtainer 310 may track a target based on a change of an electrode signal sensed from a plurality of electrodes due to movement of the target in the object.

In detail, the data obtainer 310 may include an electrocardiography device (not shown). According to an exemplary embodiment, the data obtainer 310 of the X-ray apparatus 300 may include a plurality of electrodes 311 for ECG attached to an object, and may obtain position information of a target based on an electrocardiogram signal sensed from the plurality of electrodes for ECG. Hereinafter, an exemplary embodiment will be described, in which the data obtainer 310 includes an ECG device including a plurality of electrodes. A target may be formed of any kind of electroconductive materials that are insertable into an object. For example, a target may be a catheter. A plurality of electrodes included in the data obtainer 310 are attached to a body portion, which is an object of X-ray imaging, and may sense an electrode signal at the position attached to the body portion. An X-ray image according to an exemplary embodiment may include a fluoroscopy image.

In detail, when a target is inserted into an object, position information of the object may be obtained based on an electrode signal sensed from a plurality of electrodes included in the data obtainer 310. For example, when a plurality of electrodes are attached to an object, an electrode close to a target may sense a greater change than an electrode that is far from the target. Accordingly, the data obtainer 310 may determine that a target is located close to electrodes that have sensed a relatively great change in an electrode signal. A position of a target may be accurately detected by comparing sizes of the plurality of electrode signals respectively sensed from the plurality of electrodes.

By using electrodes for ECG, the X-ray apparatus 300 according to an exemplary embodiment may capture an X-ray image or a fluoroscopy image by tracking a target according to the user's intention without any additional structure or particular manipulation by a user besides a structure of a typical X-ray apparatus. Accordingly, the X-ray apparatus 300 may provide an efficient environment to the user.

The X-ray apparatus 300 may measure an electrocardiogram of an object or a patient while monitoring angiography or medical treatment such as surgical treatment by using electrodes for ECG. Accordingly, the X-ray apparatus 300 may provide an efficient environment to the user.

According to an exemplary embodiment, the controller 320 of the X-ray apparatus 300 may set first coordinates with respect to an object and second coordinates with respect to an X-ray image.

The first coordinates may indicate an absolute position of a target in the object. That is, the first coordinates may be an actual position of the target. The controller 320 may set the first coordinates based on position information of the target obtained from the data obtainer 310. Alternatively, the first coordinate setter 321 included in the controller 320 according to an exemplary embodiment may set first coordinates.

The second coordinates may indicate a relative position of an object in an X-ray image. That is, second coordinates may be a position in an X-ray image. In detail, the controller 320 may transform the first coordinates to the second coordinates through an operation whereby the first coordinates are multiplied by a geometric transform matrix (hereinafter referred to as 'M'). Alternatively, the second coordinate setter 322 included in the controller 320 according to an exemplary embodiment may set second coordinates.

According to an exemplary embodiment, the controller 320 of the X-ray apparatus 300 may adjust the collimator 330 more efficiently based on the second coordinates, which reflect a relative position of the target, than the first coordinates, which reflect an absolute position of the target, because a second coordinate system which is a reference for the second coordinates may be based on an X-ray imaging environment.

The controller 320 may adjust a position of the collimator 330 based on the second coordinates. That is, the controller 320 may adjust the collimator 330 such that an X-ray is irradiated while a target is being tracked. Accordingly, the user may efficiently monitor a medical treatment. In detail, by using the X-ray apparatus 300 according to an exemplary embodiment, the user may obtain a fluoroscopy image of an object that is captured while tracking a target.

The X-ray apparatus 300 is not limited to the above configuration. For example, the plurality of electrodes 311 and the data obtainer 310 may be included in the controller 320. The controller 320 may not be divided into the first coordinate setter 321 and the second coordinates setter 322.

In detail, according to an exemplary embodiment, the X-ray apparatus 300 may include the collimator 330 that adjusts an X-ray irradiation region and the controller 320 that obtains position information of a target in an object based on an electrode signal sensed from the plurality of electrodes 311 attached to the object and adjusts a position of the collimator 330 based on the position information of the target.

That is, the X-ray apparatus 300 may track a target by directly adjusting the collimator 330 based on position information based on an electrode signal sensed from a plurality of electrodes.

Figure 4:
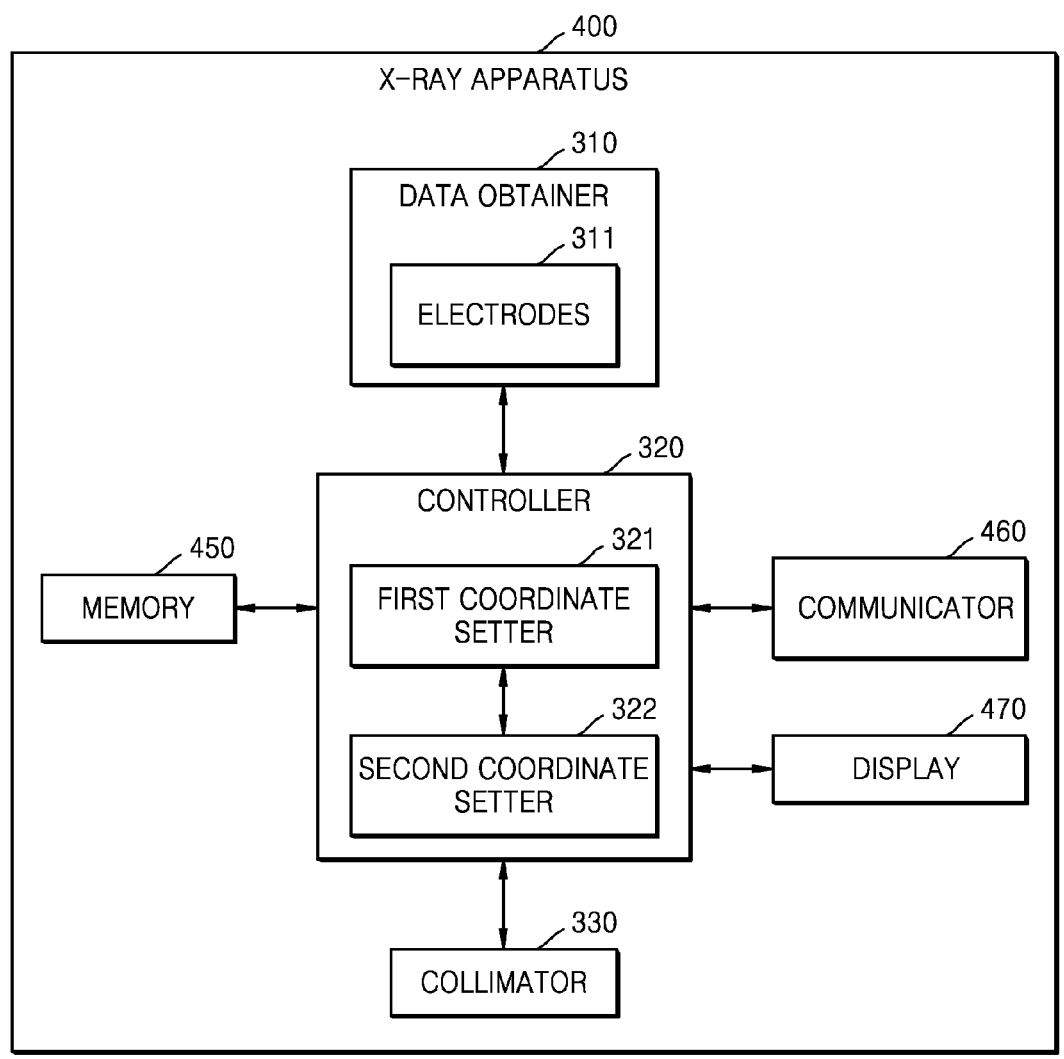
FIG. 4 illustrates a structure of an X-ray apparatus according to another exemplary embodiment.

FIG. 4 illustrates a structure of an X-ray apparatus 400 according to another exemplary embodiment. The X-ray apparatus 400 further includes at least one of a memory 450 and a communicator 460, as compared to the X-ray apparatus 300, and may be included into the X-ray apparatus 100 or separately provided.

The descriptions provided regarding the X-ray apparatus 300 are applicable to the X-ray apparatus 400 and will not be repeated.

The memory 450 may store various types of data related to an X-ray image and/or a captured X-ray image. In detail, the memory 450 may store a first X-ray image, which is captured before an ROI is adjusted by the controller 320, and a second X-ray image, which is captured after the ROI is adjusted. Also, the memory 450 may store a third X-ray image generated by the controller 320 by combining the first X-ray image and the second X-ray image.

The memory 450 may store position information of a target. In detail, the memory 450 may store an electrode signal sensed from a plurality of electrodes, position information, and first and second coordinates of the target.

The communicator 460 may transmit or receive data via a wired or wireless network to or from an external device. For example, if the X-ray apparatus 400 is included in the X-ray apparatus 100 illustrated in FIG. 1, the communicator 460 may transmit and/or receive predetermined data to or from an external server 162, an external medical apparatus 164, and/or an external portable terminal 166 which are outside the X-ray apparatus 400.

A display 470 may display an X-ray image generated according to X-ray imaging. The display 470 may correspond to the output unit described above with reference to FIG. 1, and the descriptions provided with reference to FIG. 1 apply to the present exemplary embodiment and will not be repeated.

Figure 5:
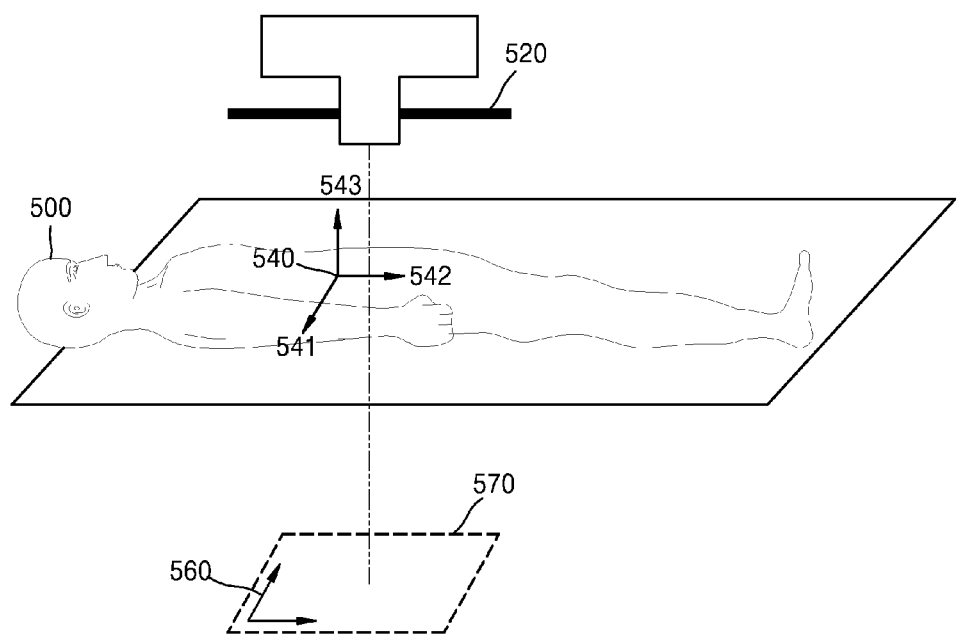
FIG. 5 is a view for explaining an operation of an X-ray apparatus according to an exemplary embodiment.

FIG. 5 is a view for explaining an operation of the X-ray apparatus 300 or 400 according to an exemplary embodiment. In detail, FIG. 5 illustrates an operation of the X-ray apparatus 300 or 400 before a target is inserted into an object 500.

According to an exemplary embodiment, a first coordinate system 540 of FIG. 5 may be a coordinate system with respect to the object 500. That is, the first coordinate system 540 may be a reference for setting first coordinates indicating an absolute position of a target in an object.

According to an exemplary embodiment, an origin and an axis of the first coordinate system 540 may be determined based on a plurality of electrodes attached to the object 500.

For example, the first coordinate system of FIG. 5 may be a 3D rectangular coordinate system based on a plurality of electrodes attached to positions corresponding to three axes 541, 542, and 543 that are orthogonal to one another.

Also, in order that the first coordinate system 540 includes all ROIs, a plurality of electrodes including the ROIs may be attached to an object.

According to an exemplary embodiment, a second coordinate system 560 of FIG. 5 may be a coordinate system with respect to an X-ray image. That is, the second coordinate system 560 may be a reference for setting second coordinates indicating a position of a target in the X-ray image.

According to an exemplary embodiment, the second coordinate system 560 may be based on an X-ray imaging environment. For example, the second coordinate system 560 of FIG. 5 may be a 2D rectangular coordinate system with respect to a 2D X-ray imaging image. An origin of the second coordinate system 560 of FIG. 5 may be located on a predetermined plane 570 corresponding to the X-ray image.

In order for an X-ray image to track a target, the X-ray apparatus 300 or 400 may adjust the collimator 520 more efficiently when based on second coordinates rather than first coordinates.

Figure 6:
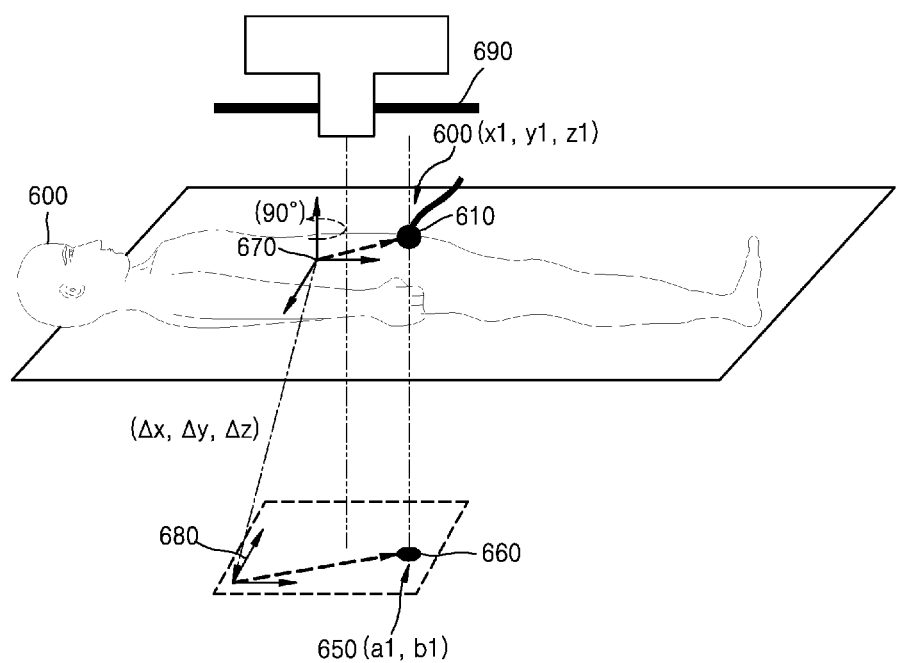
FIG. 6 is a view for explaining an operation of an X-ray apparatus according to an exemplary embodiment.

FIG. 6 is a view for explaining an operation of the X-ray apparatus 300 or 400 according to an exemplary embodiment. In detail, FIG. 6 illustrates an operation of the X-ray apparatus 300 or 400 before the controller 320 adjusts a collimator 690 after a target 610 is inserted into an object. A first coordinate system 670 and a second coordinate system 680 of FIG. 6 may respectively correspond to the first coordinate system 540 and the second coordinate system 560 of FIG. 6. Thus, the descriptions provided with reference to FIG. 5 apply to the present exemplary embodiment.

According to an exemplary embodiment, the target 610 of the X-ray apparatus 300 or 400 may be a tip of a catheter inserted into the object.

The X-ray apparatus 300 or 400 may adjust the collimator 690 based on a position of the catheter inserted into the object. Accordingly, when performing angiography, the user may efficiently monitor a fluoroscopy image.

According to an exemplary embodiment, after the target 610 is inserted into the object, the data obtainer 310 of the X-ray apparatus 300 or 400 may obtain position information of the target 610 in the object based on an electrode signal sensed from a plurality of electrodes attached to the object. In detail, a position of the target 610 may be determined by comparing electrode signals sensed from a plurality of electrodes before and after the target 610 is inserted. For example, the closer a predetermined electrode is to the insertion position, the greater a change may be generated in an electrode signal sensed from the electrode.

According to an exemplary embodiment, the controller 320 of the X-ray apparatus 300 or 400 may set first coordinates 600 indicating a position of the target 610 on the first coordinate system 670 with respect to the object, based on position information of the target. For example, the controller 320 may set the first coordinates 600 of FIG. 6 to (x1, y1, and z1).

The first coordinates 600 may accurately indicate a position of the target based on an X-ray irradiation region adjusted by a collimator. In detail, the narrower the X-ray irradiation area, the more precisely the first coordinate system 670 may be divided in order to accurately track the target. Accordingly, the first coordinates 600 may accurately indicate the position of the target. That is, according to an exemplary embodiment, the user may adjust a size of an X-ray irradiation region, and the controller 320 may adjust a degree of precision of the division of the first coordinate system 670 based on the X-ray irradiation region.

According to an exemplary embodiment, the controller 320 of the X-ray apparatus 300 or 400 may transform the first coordinates 600 to a second coordinates 650 on the second coordinate system 680. For example, the controller 320 may transform the first coordinates (x1, y1, z1) of FIG. 6 to set the second coordinates 650 to (a1, b1). As described above, the second coordinates 650 may indicate a position 660 of a target indicated in an X-ray image.

In detail, the controller 320 may transform the first coordinates 600 to the second coordinates 650 through a matrix M.

$$\begin{bmatrix} a1 \\ b1 \\ c1 \\ 1 \end{bmatrix} = M \begin{bmatrix} x1 \\ y1 \\ z1 \\ 1 \end{bmatrix} \qquad \text{[Equation 1]}$$

According to an exemplary embodiment, the controller 320 may set c1 in order to adjust dimensions of the first coordinates 600 and the second coordinates 650. Thus, c1 may be an arbitrary value for convenience of calculation. For example, c1 may be 0 or the same value as z1.

That is, the controller 320 transforms the first coordinates 600 of FIG. 6, which are 3D, to the second coordinates 650, which are 2D, and thus the controller 320 does not specify a value of c1.

According to an exemplary embodiment, the M may be defined by Equation 2.

$$M = T \cdot S \cdot R_x \cdot R_y \cdot R_z \qquad \text{[Equation 2]}$$

$$T \cdot S = \begin{bmatrix} S_x & 0 & 0 & \Delta x \\ 0 & S_y & 0 & \Delta y \\ 0 & 0 & S_z & \Delta z \\ 0 & 0 & 0 & 1 \end{bmatrix} \quad R_x = \begin{bmatrix} 1 & 0 & 0 & 0 \\ 0 & \cos\alpha & \sin\alpha & 0 \\ 0 & -\sin\alpha & \cos\alpha & 0 \\ 0 & 0 & 0 & 1 \end{bmatrix}$$

$$R_y = \begin{bmatrix} \cos\beta & 0 & -\sin\beta & 0 \\ 0 & 1 & 0 & 0 \\ \sin\beta & 0 & \cos\beta & 0 \\ 0 & 0 & 0 & 1 \end{bmatrix} \quad R_z = \begin{bmatrix} \cos\gamma & \sin\gamma & 0 & 0 \\ -\sin\gamma & \cos\gamma & 0 & 0 \\ 0 & 0 & 1 & 0 \\ 0 & 0 & 0 & 1 \end{bmatrix}$$

Here, a transition matrix T may be a matrix for transitioning an origin of the first coordinate system 670 to an origin of the second coordinate system 680. In detail, the transition matrix T may move the first coordinates 600 by ($\Delta x$, $\Delta y$, $\Delta z$).

A scale matrix S may be a matrix for transforming a scale of x, y, and z axes of the first coordinate system 670 to a scale of a and b axes of the second coordinate system 670. In detail, the scale matrix S may transform x, y, and z axes of the first coordinates 600 by magnifications of $S_x$, $S_y$, and $S_z$, respectively.

A rotation matrix $R_x$, $R_y$, and $R_z$ may be a matrix for rotating the first coordinate system 670 clockwise with respect to the x, y, and z axes. In detail, the first coordinate system 670 may be rotated clockwise by $\alpha$, $\beta$, and $\gamma$ with respect to the x, y, and z axes based on Equation 2.

For example, if the first coordinates 600 and the second coordinates 650 correspond to each other, the M may be a unit matrix.

Alternatively, if the first coordinate system 670 and the second coordinate system 680 correspond to each other, and positions of origins and axis scales of the first and second coordinate systems 670 and 680 are different, the controller 320 may set the second coordinates 650 as in Equation 3.

$$\begin{bmatrix} a1 \\ b1 \\ c1 \\ 1 \end{bmatrix} = T \cdot S \cdot I \cdot \begin{bmatrix} x1 \\ y1 \\ z1 \\ 1 \end{bmatrix} \quad \text{[Equation 3]}$$

$$a1 = S_x \cdot x1 + \Delta x$$
$$b1 = S_y \cdot y1 + \Delta y$$

Alternatively, if the first coordinate system 670 and the second coordinate system 680 are different by $\gamma$ in x-axis and y-axis directions with respect to a z-axis, and positions of origins and axis scales of the first and second coordinate systems 670 and 680 are different, the controller 320 may set the second coordinates 650 as in Equation 4.

$$\begin{bmatrix} a1 \\ b1 \\ c1 \\ 1 \end{bmatrix} = T \cdot S \cdot R_z \cdot \begin{bmatrix} x1 \\ y1 \\ z1 \\ 1 \end{bmatrix} \quad \text{[Equation 4]}$$

$$a1 = S_x \cdot (\cos\gamma \cdot x1 + \sin\gamma \cdot y1) + \Delta x$$
$$b1 = S_y \cdot (-\sin\gamma \cdot x1 + \cos\gamma \cdot y1) + \Delta y$$

Alternatively, the controller 320 may rotate the first coordinate system 670 of FIG. 6 counterclockwise by 90° ($\gamma = -90°$) with respect to a z-axis, transition an origin of the first coordinate system 670 and transform a scale of the first coordinate system 670 to thereby set the second coordinates 650 according to Equation 5.

$$a1 = S_x \cdot y1 + \Delta x$$
$$b1 = -S_y \cdot x1 + \Delta y \quad \text{[Equation 5]}$$

However, a method of setting the second coordinates 650 by the controller 320 is not limited thereto. A method of setting the second coordinates 650 by the controller 320 according to other exemplary embodiments will be described in detail with reference to FIGS. 9 and 10.

According to an exemplary embodiment, the controller 320 may set the M based on Equation 6.

$$\text{Arg}_M \min(\text{DATA2} - M \cdot \text{DATA1}) \quad \text{[Equation 6]}$$

Here, DATA1 may be data of a first coordinate system, and DATA2 may be data of a second coordinate system. That is, the controller 320 may set the M to a value that minimizes a feature difference between data of the second coordinate system and data obtained by transforming data of the first coordinate system.

For example, DATA1 may be an origin of the first coordinate system, and DATA2 may be an origin of the second coordinate system. The controller 320 may set the M to a value that may minimize a feature difference between DATA2, which is the origin of the second coordinate system, and M·DATA1, which is obtained by transforming the origin of the first coordinate system, DATA1.

Alternatively, DATA1 and DATA2 may be values set by a user in advance based on an imaging environment.

In detail, according to an exemplary embodiment, the controller 320 may use, for example, a 1 norm based pseudo inverse solution method or a 2 norm based gradient method in order to obtain the M.

Figure 7:
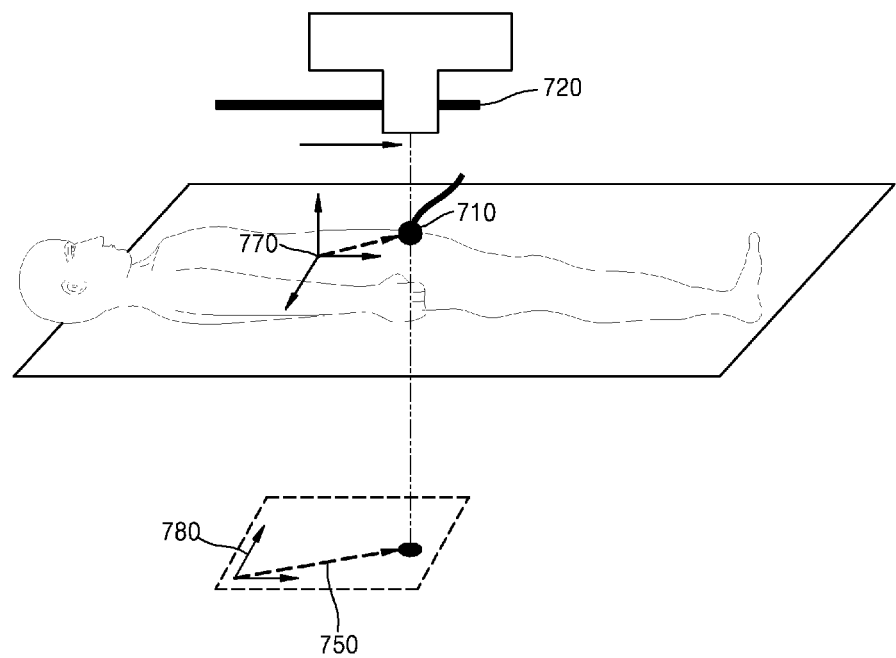
FIG. 7 is a view for explaining an operation of an X-ray apparatus according to an exemplary embodiment.

FIG. 7 is a view for explaining an operation of an X-ray apparatus according to an exemplary embodiment. In detail, FIG. 7 illustrates an operation of the X-ray apparatus 300 or 400 that adjusts the collimator 720 after a target 710 is inserted into an object. A first coordinate system 770 and a second coordinate system 780 of FIG. 7 may respectively correspond to the first coordinate system 670 and the second coordinate system 680 of FIG. 6. Thus, descriptions provided with reference to FIG. 6 apply to the present exemplary embodiment and will be omitted.

According to an exemplary embodiment, the controller 320 may adjust a position of a collimator 720 based on second coordinates 750. For example, the controller 320 may adjust a position of the collimator 720 so that the second coordinates 750 are located in a center of an X-ray irradiation region.

According to an exemplary embodiment, the controller 320 may adjust an intensity of an X-ray based on the X-ray irradiation region by using the collimator 720. The greater the X-ray irradiation region, the higher may be the intensity of the X-ray.

According to an exemplary embodiment, the controller 320 may adjust an irradiation timing of an X-ray based on a control timing of the collimator 720, such that after the collimator 720 is adjusted, an X-ray is irradiated.

The controller 320 may adjust a size of an X-ray irradiation region by using the collimator 720 based on an imaging environment such as a movement speed or a size of a target.

Figure 8:
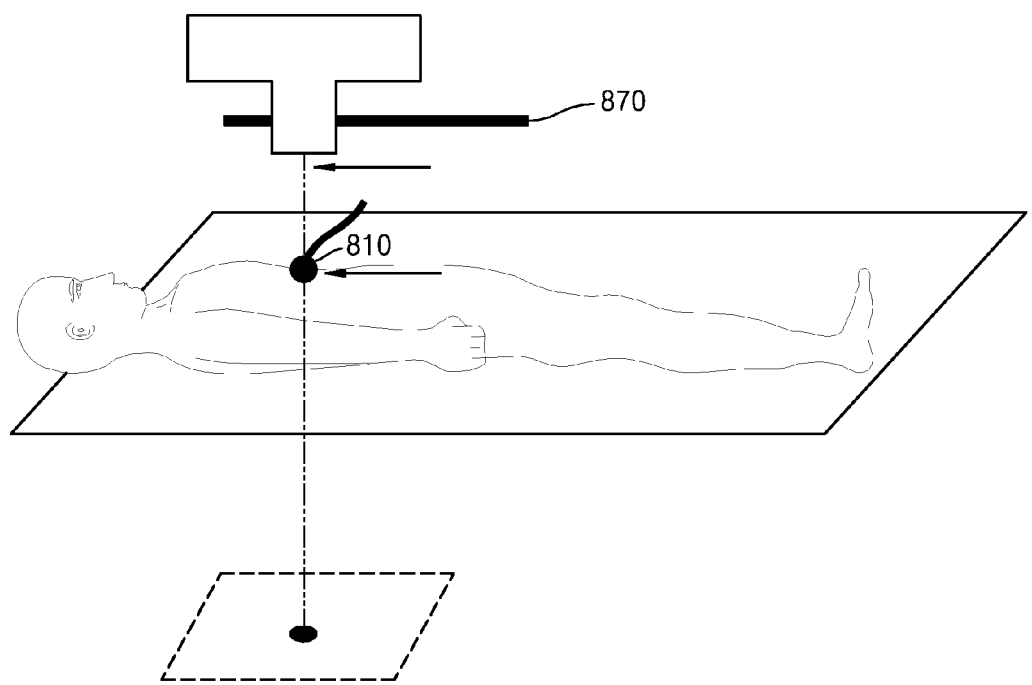
FIG. 8 is a view for explaining an operation of an X-ray apparatus according to an exemplary embodiment.

FIG. 8 is a view for explaining an operation of an X-ray apparatus according to an exemplary embodiment. In detail, FIG. 8 illustrates an operation, performed by the X-ray apparatus 300 or 400, of adjusting the collimator 870 as a target 810 in an object moves. First coordinates and second coordinates of FIG. 8 may respectively correspond to the first coordinates 600 and the second coordinates 650 of FIG. 6. Thus, descriptions provided with reference to FIG. 6 apply to the present exemplary embodiment and will be omitted.

According to an exemplary embodiment, the controller 320 may adjust a position of a collimator with respect to a direction along which the second coordinates move.

For example, as the target 810 in the object of FIG. 8 moves to the left, the controller 320 may set first coordinates and second coordinates and may move a collimator 870 to the left based on the second coordinates.

According to an exemplary embodiment, the controller 320 may generate a fluoroscopy image whereby a target is tracked based on the first and second coordinates and by using the collimator 870.

The X-ray apparatus captures the fluoroscopy image by tracking the target 810, thereby providing an efficient fluoroscopy image and an efficient surgical treatment environment.

Figure 9:
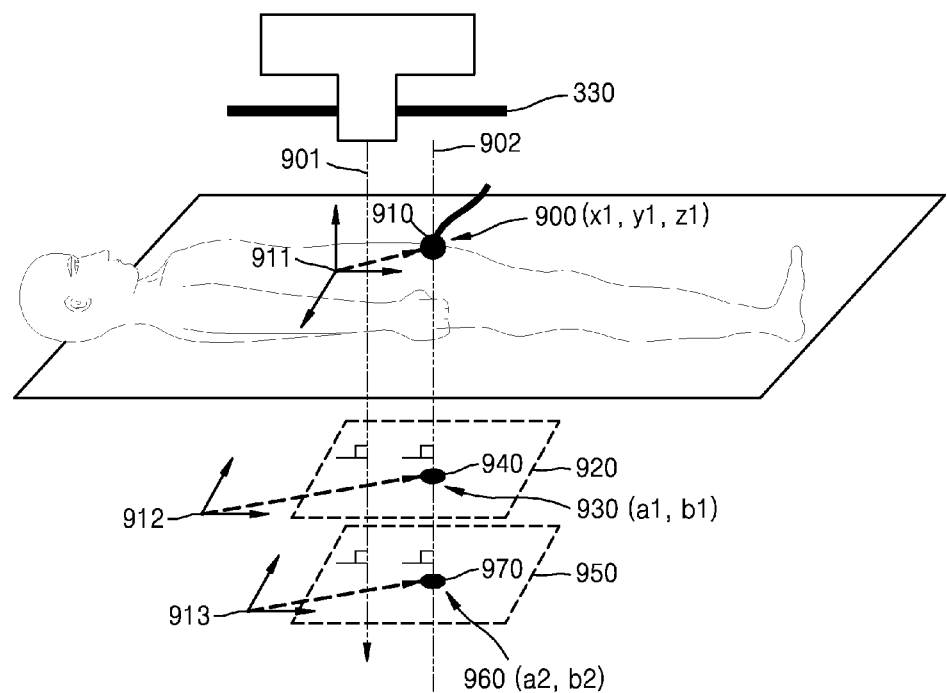
FIG. 9 is a view for explaining an operation of an X-ray apparatus according to an exemplary embodiment.

FIG. 9 is a view for explaining an operation of an X-ray apparatus according to an exemplary embodiment. In detail, FIG. 9 illustrates an operation of the X-ray apparatus 300 or 400 before the controller 320 adjusts the collimator 330 after a target 910 is inserted into an object.

According to an exemplary embodiment, the controller 320 may set a first coordinate system 911 to a 3D rectangular coordinate system based on electrode signals sensed from a plurality of electrodes attached to positions respectively corresponding to three axes that are orthogonal to one another. The controller 320 may set second coordinate systems 912 and 913 to 2D rectangular coordinate systems which are planes 920 and 950 perpendicular to an X-ray irradiation direction 901. The controller 320 may set the second coordinates 930 and 960 to points 940 and 970 on the planes 920 and 950 that are closest to the first coordinates 900.

According to an exemplary embodiment, the controller 320 may set values of the first coordinates 900 of FIG. 9 to (x1, y1, and z1).

According to an exemplary embodiment, the first coordinate system 911 which is a reference for the first coordinates 900 may be independent from the X-ray irradiation direction 901, and the second coordinate systems 912 and 913 which are a reference for the second coordinates 930 and 960 may depend on the X-ray irradiation direction 901. Accordingly, the controller 320 may adjust the collimator 330 more efficiently by tracking a target when based on the second coordinates 930 and 960 than the first coordinates 900.

In detail, origins of the second coordinate systems 912 and 913 of FIG. 9 may be placed on the planes 920 and 950 which are perpendicular to the X-ray irradiation direction 901. The origins of the second coordinate systems 912 and 913 may be at any points on the planes 920 and 950 based on an X-ray imaging environment including positions of an X-ray source, a collimator, and an object.

A specific position of the planes 920 and 950 may be set based on the X-ray imaging environment. For example, the planes 920 and 950 may be located in a detector of the X-ray apparatus.

According to an exemplary embodiment, the second coordinate systems 912 and 913 may respectively include two axes that are orthogonal to each other on the planes 920 and 950. Accordingly, the second coordinate systems 912 and 913 may be 2D rectangular coordinate systems on the planes 920 and 950.

According to an exemplary embodiment, the controller 320 may respectively set the second coordinates 930 and 960 to points 940 and 970 on the planes 920 and 950 that are closest to the first coordinates 900. In detail, the controller 320 may respectively set the second coordinates 930 and 960 to the points 940 and 970 that pass through the first coordinates 900 and at which a line 902 perpendicular to the planes 920 and 950 and extending in the same direction as the X-ray irradiation direction 901 crosses the planes 920 and 950.

According to an exemplary embodiment, the controller 320 may set values of the second coordinates 930 and 960 to (a1, b1) and (a2, b2), respectively.

The second coordinates 930 and 960 of FIG. 9 may be the same point as the second coordinates 650 of FIG. 6 or different.

Figure 10:
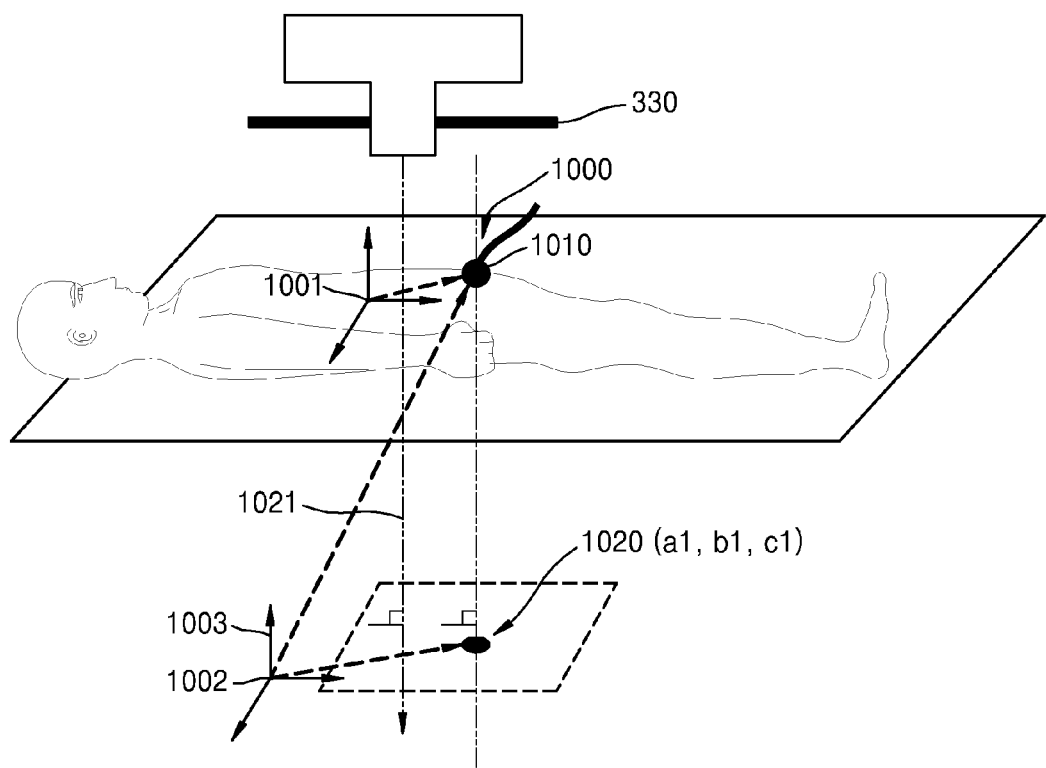
FIG. 10 is a view for explaining an operation of an X-ray apparatus according to an exemplary embodiment.

FIG. 10 is a view for explaining an operation of an X-ray apparatus according to an exemplary embodiment. FIG. 10 illustrates an operation of the X-ray apparatus 300 or 400 before the controller 320 adjusts the collimator 330 after a target 1010 is inserted into an object.

According to an exemplary embodiment, the controller 320 may set a first coordinate system 1001 to a 3D rectangular coordinate system based on an electrode signal sensed from a plurality of electrodes attached to positions corresponding to three axes that are orthogonal to one another, and may set a second coordinate system 1002 to a 3D rectangular coordinate system including an axis 1003 which is in the same direction as an X-ray irradiation direction 1021.

The controller 320 may set the axis 1003 which is in the same direction as the X-ray irradiation direction 1021 as a z-axis of the second coordinate system 1002 of FIG. 10. Thus, second coordinates 1020 may indicate an absolute position of a target in an object, similarly to the first coordinates 1000. That is, the second coordinates 1020 may be an actual position of the target in the object.

For example, the controller 320 may set a value of the second coordinates 1020 to (a1, b1, and c1). The controller 320 may set c1, which is a z-axis component of the second coordinates 1020 of FIG. 10, as a value corresponding to the actual position of the target.

However, according to an exemplary embodiment, the second coordinates 1020 of FIG. 10 may still depend on the X-ray irradiation direction 1021, and thus, the controller 320 may adjust the collimator 330 more efficiently when based on the second coordinates 1020 than the first coordinates 1000.

Figure 11A:
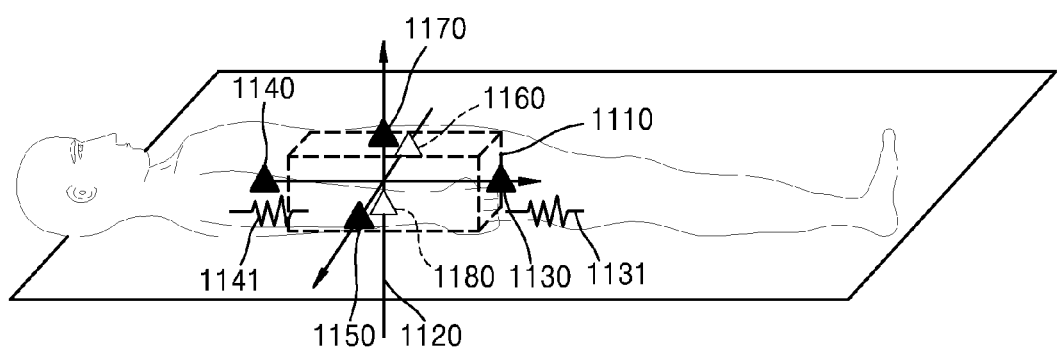
FIGS. 11A and 11B are views for explaining an operation of an X-ray apparatus according to an exemplary embodiment.
Figure 11B:
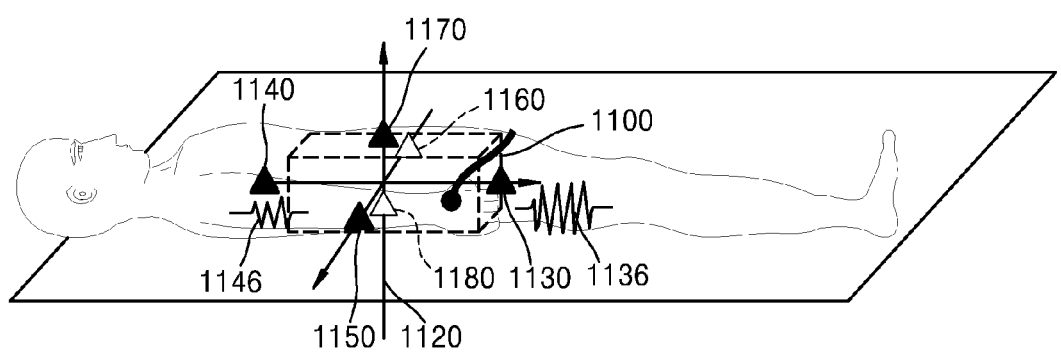

FIGS. 11A and 11B are views for explaining an operation of an X-ray apparatus according to an exemplary embodiment. FIGS. 11A and 11B illustrate an operation of the data obtainer 310 of the X-ray apparatus 300 or 400 to obtain position information of a target based on an electrode signal sensed from a plurality of electrodes.

The data obtainer 310 according to an exemplary embodiment may include a plurality of electrodes 1130, 1140, 1150, 1160, 1170, and 1180 for ECG attached to an object, and may obtain position information of a target in an object based on electrocardiogram signals 1131, 1141, 1136, and 1146 sensed from the electrodes for ECG.

For example, two electrodes 1130 and 1140 are attached to positions corresponding to an x-axis, two electrodes 1150 and 1160 are attached to positions corresponding to a y-axis, and two electrodes 1170 and 1180 are attached to positions corresponding to a z-axis. Thus, the first coordinate system 1120 may be a 3D rectangular coordinate system based on the positions of the plurality of electrodes described above.

FIG. 11A illustrates electrocardiogram signals 1131 and 1141 sensed from a plurality of electrodes before a target is inserted into an object which may be stable and/or substantially similar. Thus, the data obtainer 310 may determine that no target has been inserted into the object.

FIG. 11B illustrates electrocardiogram signals 1136 and 1146 sensed from a plurality of electrodes after a target is inserted into an object.

For example, a change may be generated in the electrocardiogram signals 1136 and 1146 sensed from a plurality of electrodes of FIG. 11B. In detail, a relatively large change may be generated in the electrocardiogram signal 1136 sensed from the electrode 1130 for ECG which is close to the target, and a relatively small change or no change may be generated in the electrocardiogram signal 1146 sensed from the electrode 1140 for ECG which is far from the target.

The data obtainer 310 may obtain position information of the target based on the electrocardiogram signals 1131, 1141, 1136, and 1146 sensed from the plurality of electrodes based on a change in the plurality of electrocardiogram signals generated due to insertion or movement of the target.

According to an exemplary embodiment, the data obtainer 310 may measure impedance of an object included in an ROI and obtain position information based on the impedance of the object.

For example, the data obtainer 310 may measure impedance of an object based on a current and a voltage sensed from the plurality of electrodes, and may obtain position information of the target based on an impedance change of the object due to the target.

Also, in order to obtain accurate position information of the target, the plurality of electrodes may be attached to the object such that the ROI 1110 is included in the area surrounded by the plurality of electrodes.

Figure 12A:
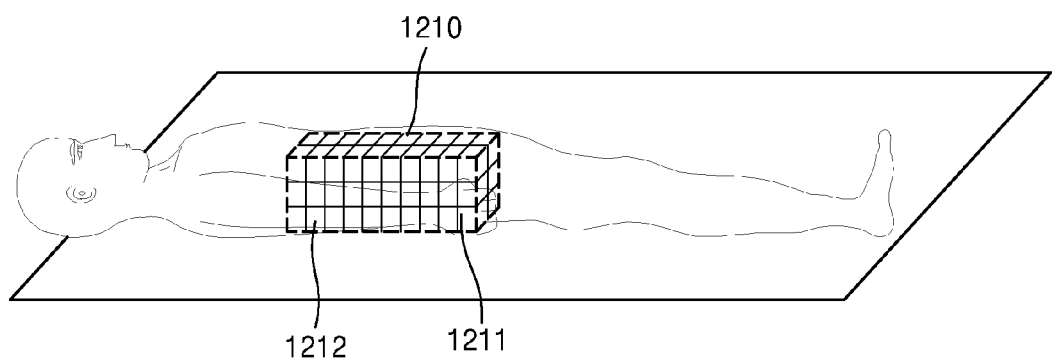
FIGS. 12A and 12B are views for explaining an operation of an X-ray apparatus according to an exemplary embodiment.
Figure 12B:
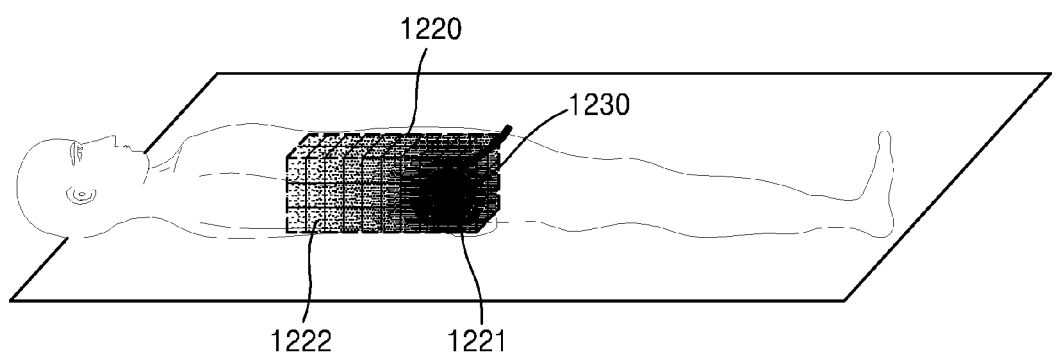

FIGS. 12A and 12B are views for explaining an operation of an X-ray apparatus according to an exemplary embodiment. FIGS. 12A and 12B illustrate an operation of the data obtainer 310 of the X-ray apparatus 300 or 400 to obtain position information of a target by using impedance maps 1210 and 1220.

According to an exemplary embodiment, the data obtainer 310 may measure impedance of an object included in an ROI based on an electrode signal described above with reference to FIGS. 11A and 11B, generate the impedance maps 1210 and 1220 of the object based on impedance of the object, and obtain position information of the target based on the impedance maps 1210 and 1220.

The impedance maps 1210 and 1220 may be data obtained by segmenting an object and measuring amplitude of impedance of each portion of the segmented object.

For example, the impedance maps 1210 and 1220 may indicate amplitude of impedance of each portion of the object. In detail, the greater the amplitude of impedance of each portion of a predetermined object, the darker may be a color of an impedance map corresponding to the portion of the object.

FIG. 12A illustrates an impedance map of an object before a target is inserted into the object. For example, impedance of each of portions 1211 and 1212 of the object included in an ROI of FIG. 12A may be uniform. Thus, the data obtainer 310 may display the impedance map 1210 of FIG. 12A in one color.

FIG. 12B illustrates an impedance map of an object after a target 1230 is inserted into the object. For example, amplitude of impedance of a portion 1221 of the object close to the target 1230 may be relatively great, and amplitude of impedance of a portion 1222 of the object farther away from the target may be relatively small. Thus, the data obtainer 310 may display the impedance map 1220 of FIG. 12B in multiple colors.

However, an operation of the data obtainer 310 to generate the impedance maps 1210 and 1220 is not limited thereto. An impedance map may include all types of data, and amplitude of impedance of each portion of an object may be measured, such as a color, a volume, a real number and a complex number.

Figure 13:
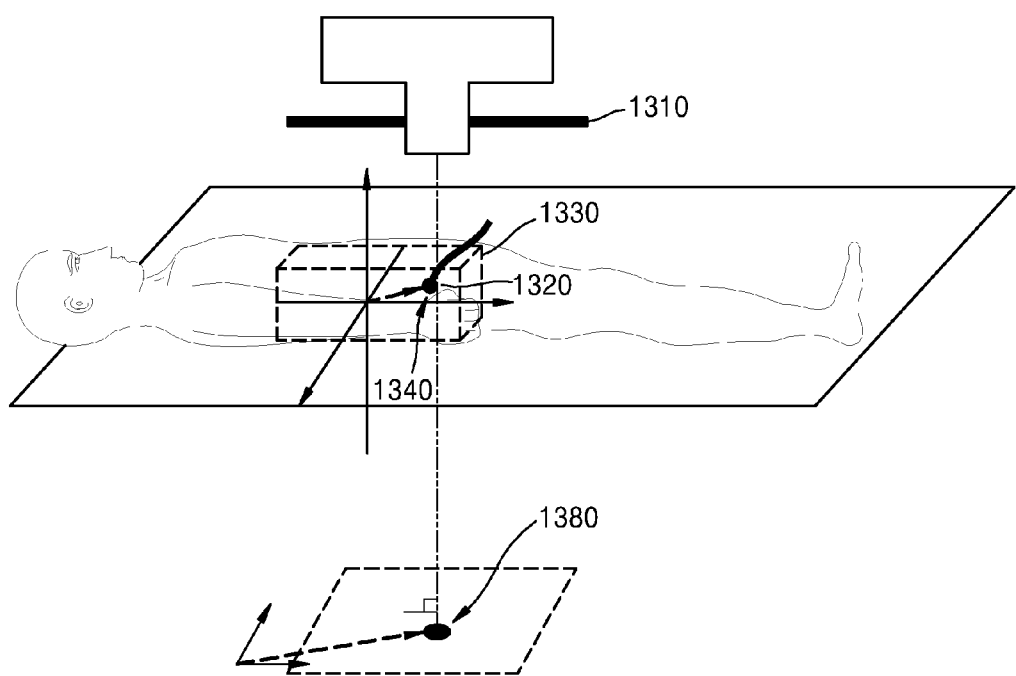
FIG. 13 is a view for explaining an operation of an X-ray apparatus according to an exemplary embodiment.

FIG. 13 is a view for explaining an operation of an X-ray apparatus according to an exemplary embodiment.

According to an exemplary embodiment, the data obtainer 310 may obtain position information of a target 1320 based on an impedance map 1330. The controller 320 may set first coordinates 1340 and second coordinates 1380 and adjust a collimator 1310 based on the position information.

Figure 12B:
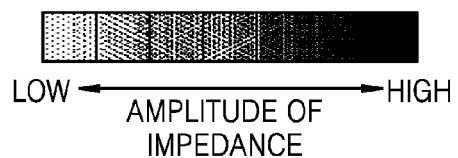

Operations of the data obtainer 310 of FIGS. 12 and 13 of generating an impedance map of an object and obtaining position information of a target may correspond to each other. An operation of the controller 320 of FIG. 13 to set first coordinates and second coordinates may correspond to the operation of the controller 320 of FIGS. 5 through 10. Thus, repeated descriptions thereof will be omitted.

Figure 14:
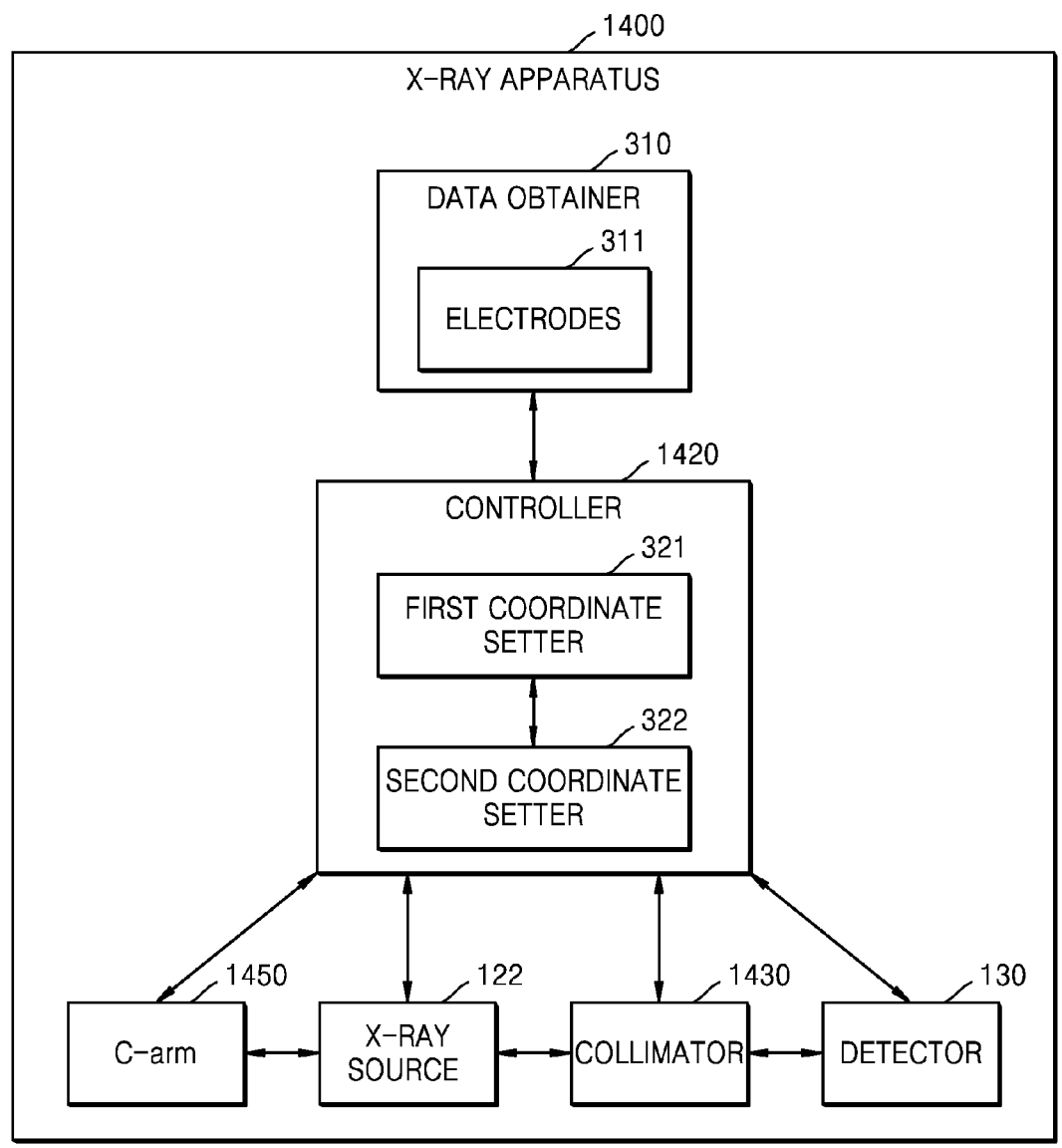
FIG. 14 illustrates a structure of an X-ray apparatus according to another exemplary embodiment.

FIG. 14 illustrates an X-ray apparatus 1400 according to an exemplary embodiment. The descriptions above provided with reference to FIGS. 1 to 4 which are applicable here will not be repeated.

According to an exemplary embodiment, the X-ray apparatus 1400 includes a C-arm 1450 that connects the X-ray source 122 and the detector 130. A controller 1420 may set, based on an angle of the C-arm 1450 and position information of the target, first coordinates indicating a position of the target on the first coordinate system with respect to the object, transform the first coordinates to second coordinates on the second coordinate system with respect to an X-ray image of the object, and adjust a position of the collimator 1430 based on the second coordinates.

As described above, by including the C-arm 1450, the X-ray apparatus 1400 may capture an image of an object at various angles. Thus, the X-ray apparatus 1400 may provide an efficient imaging environment to a user.

The controller 1420 may efficiently set the M matrix based on an angle of the C-arm 1450, thereby setting accurate second coordinates. An operation of the controller 1420 to set the M and second coordinates based on an angle of the C-arm 1450 will be described in detail with reference to FIGS. 15 through 17.

Figure 15:
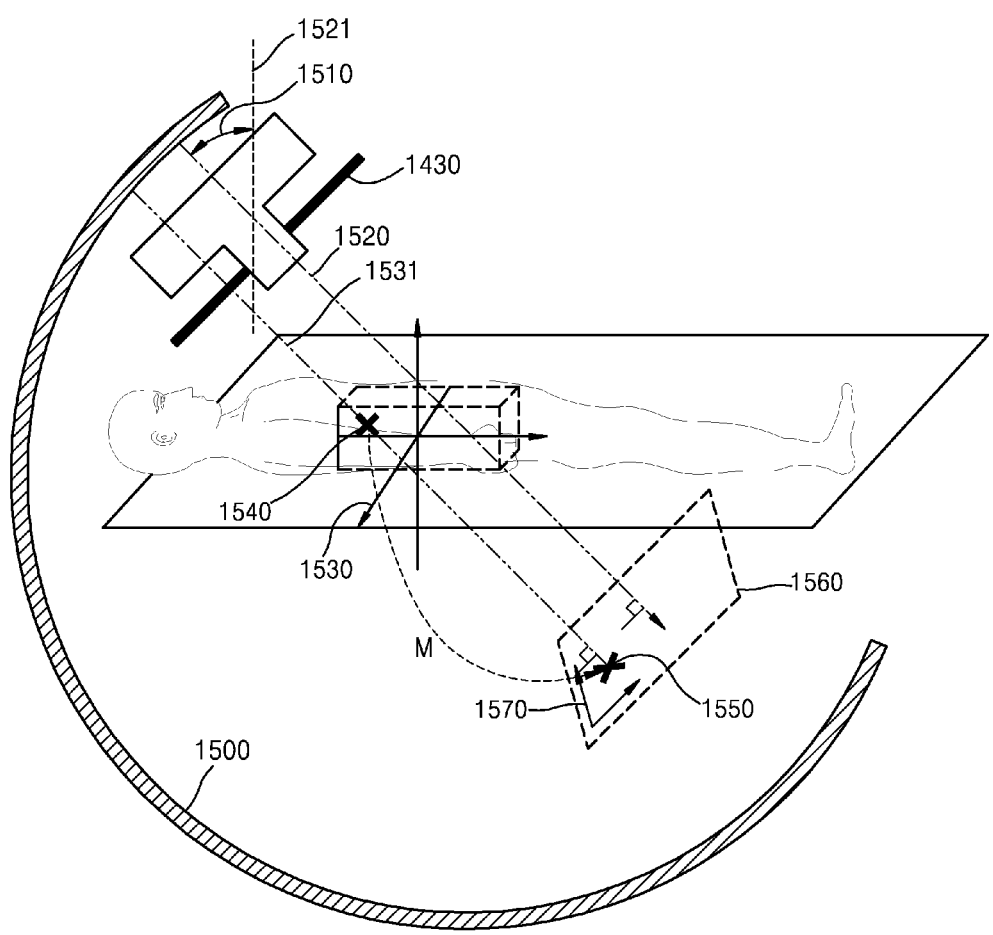
FIG. 15 is a view for explaining an operation of an X-ray apparatus according to an exemplary embodiment.

FIG. 15 is a view for explaining an operation of an X-ray apparatus according to an exemplary embodiment. FIG. 15 illustrates an operation of the controller 1420 of the X-ray apparatus including a C-arm 1500 tilted at 45 degrees, to set the M. A first coordinate system 1530 of FIG. 15 may correspond to the first coordinate system 540 of FIG. 5. Thus, descriptions provided with reference to FIG. 5 apply to the present exemplary embodiment and will be omitted.

According to an exemplary embodiment, the controller 1420 may specify an X-ray irradiation direction 1520 based on an angle 1510 of the C-arm 1500. For example, the angle 1510 may be 45 degrees, but this is not limiting. The controller 1420 may efficiently set the M based on the X-ray irradiation direction 1520. The angle 1510 of the C-arm 1500 may be an angle between a reference line 1521 and the X-ray irradiation direction 1520 according to movement of the C-arm 1500.

The controller 1420 may set a second coordinate system 1570 to a 2D rectangular coordinate system, on a plane 1560 perpendicular to the X-ray irradiation direction 1520. The controller 1420 may set a point where a line 1531 that passes through DATA1 1540 of Equation 6 and is parallel to the X-ray irradiation direction 1520 meets the plane 1560 as DATA2 1550.

As described above, DATA1 may be data of a first coordinate system. For example, DATA1 may be an origin of the first coordinate system. Alternatively, DATA1 may be a predetermined point on the first coordinate system set by a user.

The controller 1420 sets the DATA2 1550 on the plane 1560, and the DATA2 1550 may be data of the second coordinate system 1570.

The controller 1420 may set as the M a value that minimizes a difference of characteristics of DATA2 and data obtained by transforming DATA1. According to an exemplary embodiment, the controller 1420 may use a 1 norm based pseudo inverse solution method or a 2 norm based gradient method in order to calculate the M.

As described above, by adjusting at least one reference plane 1560 among the first coordinate system 1530 and the second coordinate system 1570 based on the angle of the C-arm 1500, an accurate position of a target 1540 may be obtained. In detail, by adjusting the reference plane 1560 of the second coordinate system 1570 based on the angle of the C-arm 1500 to be a plane perpendicular to an X-ray irradiation direction 1520, a more accurate position of the target 1540 may be obtained.

Figure 16:
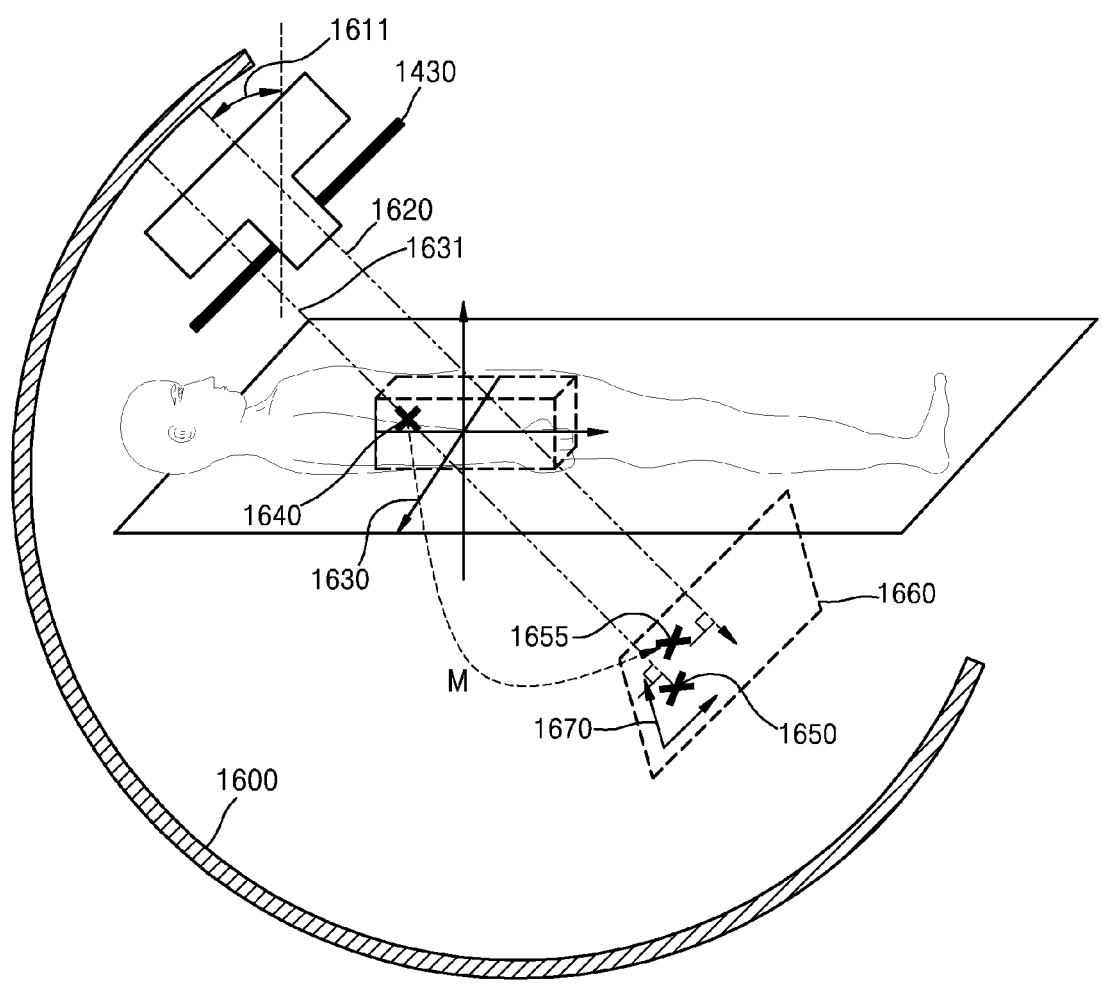
FIG. 16 is a view for explaining an operation of an X-ray apparatus according to an exemplary embodiment.

FIG. 16 is a view for explaining an operation of an X-ray apparatus including a C-arm 1600 tilted at 45 degrees, to set the M, according to an exemplary embodiment. A first coordinate system 1630 of FIG. 16 may correspond to the first coordinate system 540 of FIG. 5, and thus descriptions provided with reference to FIG. 5 apply to the present exemplary embodiment and will be omitted.

The first coordinate system 1630 and a second coordinate system 1670 of FIG. 16 may respectively correspond to the first coordinate system 1530 and the second coordinate system 1570 of FIG. 15. Thus, descriptions provided with reference to FIG. 15 and also applied to the present exemplary embodiment will be omitted.

According to an exemplary embodiment, DATA1 and DATA2 of Equation 6 may be set in advance. For example, a user may directly set DATA1 and DATA2, and the controller 1420 may set an M that minimizes a difference of characteristics of DATA2 and data obtained by transforming DATA1. As described above, the controller 1420 may specify an X-ray irradiation direction 1620 based on an angle 1611 of the C-arm 1600, and may efficiently set an M based on the X-ray irradiation direction 1620.

The user may set DATA1 1640, which is data on the first coordinate system 1630, and DATA2 1655, which is data on the second coordinate system 1670. According to an exemplary embodiment, the controller 1420 may set as DATA3 1650 a point where a line 1631 that passes through the DATA1 1640 and is parallel to the X-ray irradiation direction 1620 meets a plane 1660 The set DATA3 1650 may be data of the second coordinate system 1670.

According to an exemplary embodiment, the controller 1420 may efficiently set an M by considering a difference of characteristics of the DATA2 1655 and the DATA3 1650.

Figure 17:
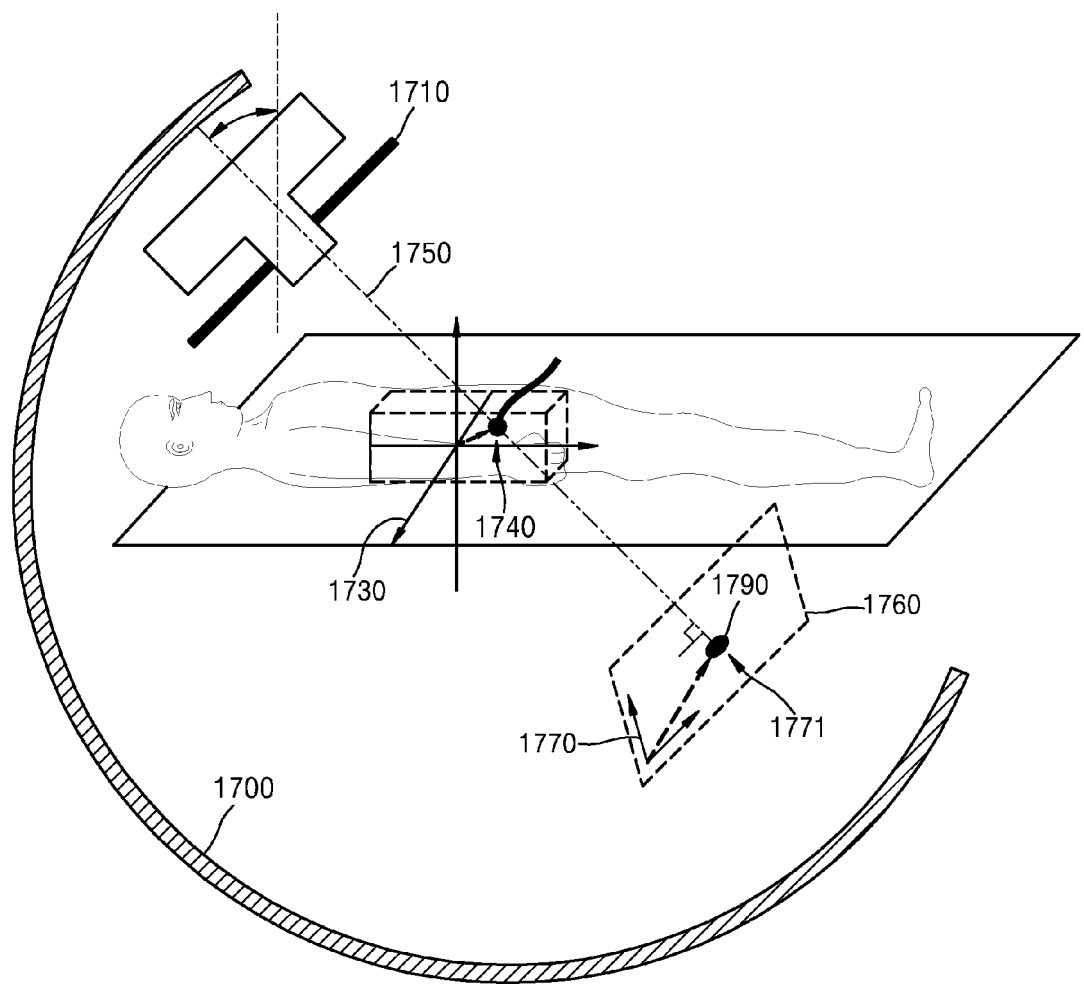
FIG. 17 is a view for explaining an operation of an X-ray apparatus according to an exemplary embodiment.

FIG. 17 is a view for explaining an operation of an X-ray apparatus according to an exemplary embodiment. In detail, FIG. 17 illustrates an operation of the controller 1420 of the X-ray apparatus 1400 including a C-arm 1700 tilted at 45 degrees, to set first coordinates 1740 and second coordinates 1771 and adjust a collimator 1710.

The first coordinate system 1730 and the second coordinate system 1770 of FIG. 17 may respectively correspond to the first coordinate system 1530 and the second coordinate system 1570 of FIG. 15. Thus, descriptions provided with reference to FIG. 15 and also applied to the present exemplary embodiment will be omitted.

As described above with reference to FIG. 6, the controller 1420 may transform the first coordinates 1740 to the second coordinates 1771 based on the M. The M of FIG. 17 may correspond to the M of FIG. 15 or the M of FIG. 16.

As in the exemplary embodiment of FIG. 9, the controller 1420 may set the second coordinates 1771 to a point on the plane 1760 that is closest to the first coordinates 1740, for example, to a point 1790 where a line 1750 that passes through the first coordinates 1740 and is in the same direction as an X-ray irradiation direction meets the plane 1760.

The second coordinates obtained by transforming the first coordinates based on the M and the second coordinates on the plane 1760 that are closest to the first coordinates may have the same value.

As in the exemplary embodiment of FIG. 7, the controller 1420 may adjust a position of the collimator 1710 based on the second coordinates 1771.

Figure 18:
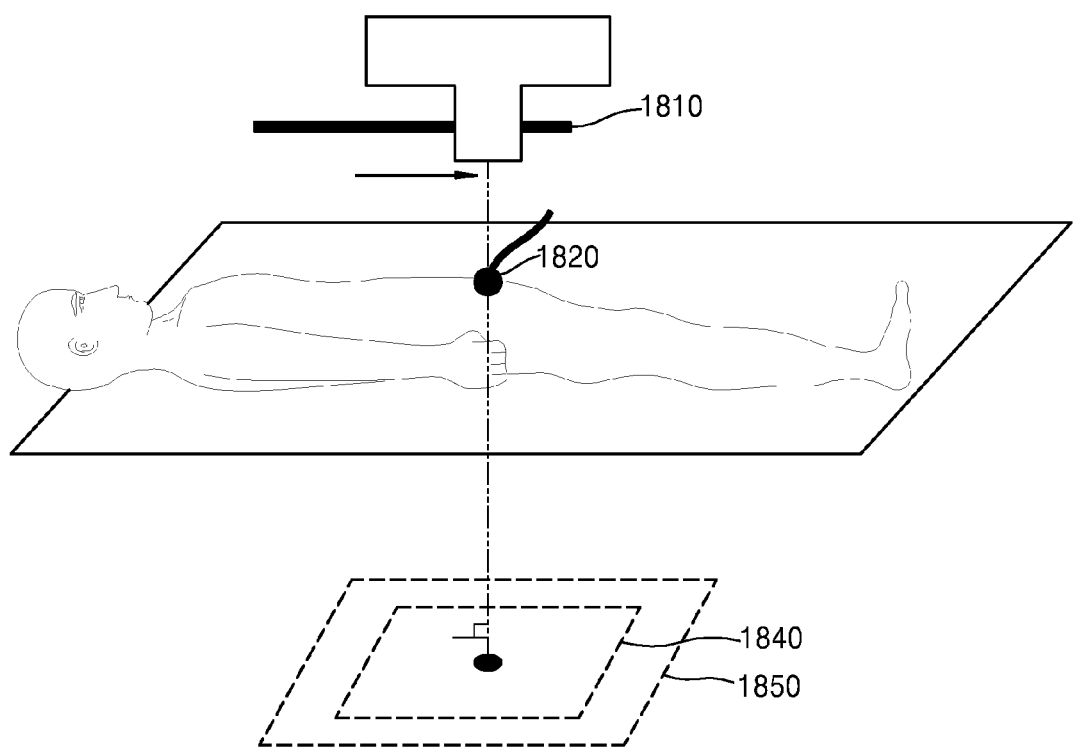
FIG. 18 is a view for explaining an operation of an X-ray apparatus according to an exemplary embodiment.

FIG. 18 is a view for explaining an operation of an X-ray apparatus according to an exemplary embodiment. First coordinates and second coordinates of FIG. 18 may respectively correspond to the first coordinates 600 and the second coordinates 650 of FIG. 6. Thus, descriptions provided with reference to FIG. 6 and also applied to the present exemplary embodiment will not be repeated.

Planes 1840 and 1850 illustrated in FIG. 18 may respectively correspond to a first X-ray image and a second X-ray image.

According to an exemplary embodiment, the controller 320 may automatically adjust an ROI based on a position of the collimator 1810, and may generate a third X-ray image by combining a first X-ray image captured before the ROI is adjusted and a second X-ray image captured after the ROI is adjusted.

For example, before a target 1820 is inserted into an object, an ROI may be relatively large in order to capture an X-ray image of the entire object. After the target 1820 is inserted into the object, an ROI may be relatively small to capture an X-ray image of only a portion around the target 1820. Accordingly, the controller 320 may combine the first X-ray image captured before the target is inserted and the second X-ray image captured after the target is inserted to provide an efficient X-ray imaging environment to a user.

Figure 19:
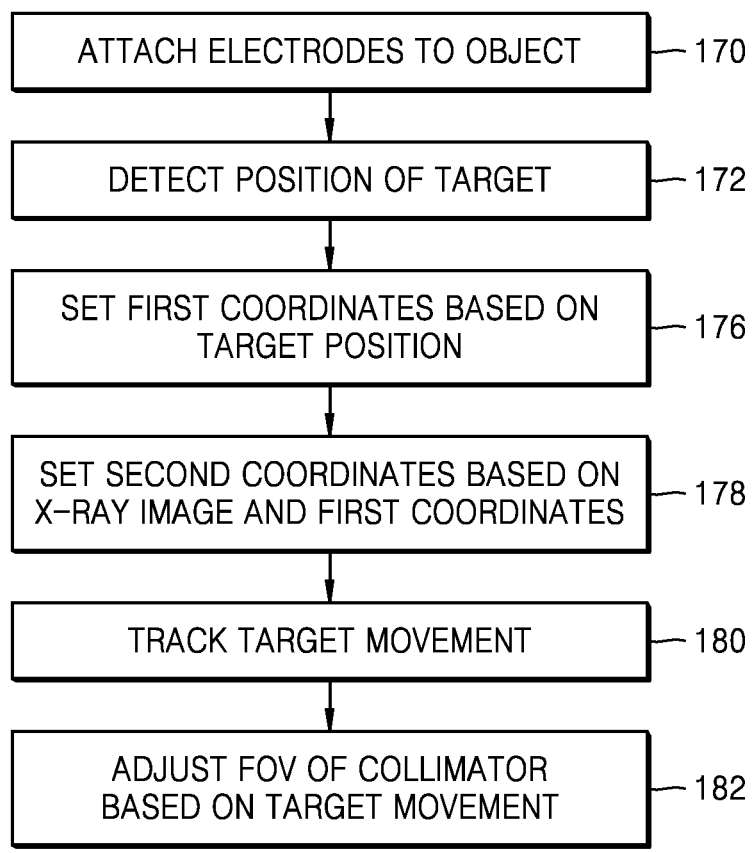
FIG. 19 is a flowchart of a method of an X-ray apparatus according to an exemplary embodiment.

FIG. 19 is a flowchart of a method of an X-ray apparatus according to an exemplary embodiment. Structure and functions of the X-ray apparatus are described in detail above and will not be repeated.

With reference to FIG. 19, the respective pairs of ECG electrodes 311 may be attached to the object, in operation 170. For example, lines drawn through respective pairs of ECG electrodes 311 may respectively correspond to x, y, and z axes orthogonal to one another. A position of a target disposed inside an object may be detected by reading out the ECG signals from corresponding pairs of the ECG electrodes, in operation 172.

The first coordinates of the detected position of the target in a first coordinate system may be determined based on the object, in operation 176. For example, the first coordinate system is set based on x, y, and z axes created in correspondence to the lines drawn through respective pairs the ECG electrodes attached to the object, and origin of the first coordinate system may coincide with the detected position of the target.

The first coordinates may be transformed into second coordinates based on a plane of an X-ray image, in operation 178. For example, the transformation may be performed such that a distance between the detected position of the target in the first coordinate system and a position of the target in the X-ray image is the shortest, in a direction parallel to the irradiation direction of the X-ray source.

A movement of the target may be tracked based on the second coordinates set based on the X-ray image, in operation 180.

A field of view (FOV) of a collimator of an X-ray source may be adjusted based on the movement of the target, in operation 182. For example, the FOV of the collimator may be adjusted by adjusting at least one of a position and an aperture of the collimator. For example, when the target includes a medical device, e.g., a catheter inserted into the object, the FOV of the collimator may be adjusted to a smallest possible degree of opening, to include only the tip of the medical device, thereby reducing a radiation exposure to the object. For example, the object may be pre-imaged such that a first X-ray image of an entire area, which is subject to the medical procedure, is obtained. After the collimator is adjusted, only a smallest possible area is irradiated with the X-rays, to reflect the movement of the medical device during the medical procedure or as desired by a doctor, and a second X-ray image is obtained in a real time or near real time. The second X-ray image may be combined with first X-ray image. The combined X-ray image may be displayed on a display for the doctor to observe a tiniest movement of the target inside a larger area of the object which has been pre-imaged.

As described above, according to exemplary embodiments, the X-ray apparatus may adjust a collimator by tracking a target based on an electrode signal. Thus, the X-ray apparatus may minimize an amount of radiation exposure to the object. Also, in angiography, a user may efficiently conduct treatment by using the X-ray apparatus according to an exemplary embodiment.

As the X-ray apparatus according to an exemplary embodiment uses electrodes for ECG, an X-ray image or a fluoroscopy image may be captured by tracking a target according to the user's intention without any other structure being added to a typical X-ray apparatus or without any particular manipulation of a user. Accordingly, the X-ray apparatus may provide an efficient imaging environment to a user.

The above-described exemplary embodiments may be written as computer programs and may be implemented in computers that execute the programs using a computer-readable recording medium.

Examples of the computer-readable recording medium include magnetic storage media (e.g., ROM, floppy disks, hard disks, etc.), optical recording media (e.g., CD-ROMs, DVDs, etc.), and transmission media such as Internet transmission media.

The foregoing exemplary embodiments and advantages are merely exemplary and are not to be construed as limiting. Descriptions of features or aspects within each exemplary embodiment should typically be considered as available for other similar features or aspects in other exemplary embodiments. Also, the description of the exemplary embodiments is intended to be illustrative, and not to limit the scope of the claims, and many alternatives, modifications, and variations will be apparent to those skilled in the art.

What is claimed is:

1. An X-ray apparatus comprising:
   a collimator configured to adjust an X-ray irradiation region; and
   a data obtainer configured to obtain position information of a target in an object based on an electrode signal sensed from electrodes attached to the object; and
   a controller configured to set first coordinates indicating a position of the target on a first coordinate system with respect to the object based on the position information, transform the first coordinates to second coordinates on a second coordinate system with respect to an X-ray image of the object, and control to adjust a position of the collimator based on the second coordinates.

2. The X-ray apparatus of claim 1, wherein the electrodes comprise electrodes for electrocardiography (ECG) that are attached to the object, and
   the electrode signal is an ECG signal.

3. The X-ray apparatus of claim 1, wherein the data obtainer is configured to measure impedance of an area of the object included in a region of interest (ROI) based on the electrode signal and obtain the position information based on the impedance of the area of the object.

4. The X-ray apparatus of claim 1, wherein the data obtainer is configured to measure impedance of an area of the object included in a region of interest (ROI) based on the electrode signal, generate an impedance map of the object based on the impedance of the area of the object, and obtain the position information based on the impedance map.

5. The X-ray apparatus of claim 1, wherein the controller is further configured to set the first coordinates to a three-dimensional (3D) rectangular coordinate system based on the electrode signal sensed from the electrodes attached to positions corresponding to three axes that are orthogonal to one another, set the second coordinate system to a two-dimensional (2D) rectangular coordinate system which is a plane perpendicular to an X-ray irradiation direction, and set a point on the plane that is closest to the first coordinates as the second coordinates.

6. The X-ray apparatus of claim 1, wherein the controller is further configured to set the first coordinate system to a three-dimensional (3D) rectangular coordinate system based on the electrode signal sensed from the electrodes attached to positions corresponding to three axes that are orthogonal to one another, and set the second coordinate system to a 3D rectangular coordinate system including an axis in a same direction as an X-ray irradiation direction.

7. The X-ray apparatus of claim 1, wherein the target is a tip of a catheter inserted in the object.

8. The X-ray apparatus of claim 1, further comprising:
   an X-ray source configured to emit an X-ray to the object;
   a detector configured to detect the X-ray transmitted through the object; and
   a C-arm configured to connect the X-ray source and the detector,
   wherein, based on an angle of the C-arm and the position information, the controller is further configured to set the first coordinates indicating the position of the target on the first coordinate system with respect to the object, transform the first coordinates to the second coordinates on the second coordinate system with respect to the X-ray image of the object, and control to adjust the position of the collimator based on the second coordinates.

9. The X-ray apparatus of claim 1, wherein the controller is configured to control to adjust the position of the collimator further based on a direction in which the second coordinates move.

10. The X-ray apparatus of claim 1, wherein the X-ray image is a first X-ray image, and
    the controller is further configured to automatically adjust a region of interest (ROI) of the object based on the position of the collimator, and generate a third X-ray image by combining the first X-ray image captured before the ROI is adjusted and a second X-ray image captured after the ROI is adjusted.

11. The X-ray apparatus of claim 1, wherein the controller is further configured to generate a fluoroscopy image that tracks a target movement in the object based on at least one among the first coordinates, the second coordinates, and the position of the collimator.

12. The X-ray apparatus of claim 1, wherein the controller is further configured to adjust an intensity of an X-ray based on the X-ray irradiation region adjusted by controlling the collimator.

13. The X-ray apparatus of claim 1, wherein the controller is further configured to adjust an irradiation timing of an X-ray based on a control timing of the collimator.

14. The X-ray apparatus of claim 1, further comprising:
    an X-ray source configured to emit an X-ray to the object;
    a detector configured to detect the X-ray transmitted through the object; and
    a C-arm configured to connect the X-ray source and the detector,
    wherein the controller is configured to control to adjust the position of the collimator further based on an angle of the C-arm.

15. The X-ray apparatus of claim 1, wherein the controller is configured to control to adjust the position of the collimator further based on a direction in which the target moves.

16. The X-ray apparatus of claim 1, wherein the controller is further configured to calculate transformation parameters between the first coordinates of the target in the first coordinate system and the second coordinates of the target in the second coordinate system, and control to adjust the position of the collimator by applying the calculated transformation parameters to the first coordinates.

17. A medical imaging method comprising:
 detecting a position of a target disposed inside an object;
 determining first coordinates of the detected position of the target in a first coordinate system which is set based on the object;
 transforming the first coordinates into second coordinates in a second coordinate system which is set based on an X-ray image;
 tracking a movement of the target based on the second coordinates; and
 adjusting a field of view (FOV) of a collimator of an X-ray source based on the movement of the target.

18. The medical imaging method of claim 17, wherein the detecting the position comprises:
 attaching pairs of electrocardiogram (ECG) electrodes to the object; and
 detecting ECG signals from corresponding pairs of ECG electrodes,
 wherein x, y, and z axes of the first coordinate system are set based on lines drawn through positions of the corresponding pairs of ECG electrodes.

19. The medical imaging method of claim 17, wherein the adjusting comprises adjusting at least one among a position of the collimator and an aperture of the collimator.

20. The medical imaging method of claim 17, wherein the target comprises a tip of a medical device inserted into the object, and
 the adjusting comprises adjusting the FOV of the collimator to include only the tip of the medical device, thereby reducing a radiation exposure to the object.

21. An X-ray apparatus, having the X-ray source configured to emit an X-ray to the object, the X-ray apparatus comprising:
 a detector configured to detect the X-ray transmitted through the object; and
 a controller configured to perform the medical imaging method of claim 17; and
 a display configured to display the X-ray image.

* * * * *